(12) United States Patent
Lee et al.

(10) Patent No.: US 11,752,204 B2
(45) Date of Patent: *Sep. 12, 2023

(54) VACCINES WITH HIGHER CARBOHYDRATE ANTIGEN DENSITY AND NOVEL SAPONIN ADJUVANT

(71) Applicant: OBI PHARMA, INC., Taipei (TW)

(72) Inventors: Wei-Han Lee, Taipei (TW); Nan-Hsuan Wang, Taipei (TW); Chung-Hao Chang, Taipei (TW); Yih-Huang Hsieh, Taipei (TW); Cheng-Der Tony Yu, Anaheim, CA (US); Cheng-Chi Wang, Taipei (TW); Yu-Hsin Lin, Taipei (TW); Yu-Chen Lin, Taipei (TW); I-Ju Chen, Taipei (TW)

(73) Assignee: OBI PHARMA INC., Taipei (TW)

( * ) Notice: Subject to any disclaimer, the term of this patent is extended or adjusted under 35 U.S.C. 154(b) by 604 days.

This patent is subject to a terminal disclaimer.

(21) Appl. No.: 16/671,395

(22) Filed: Nov. 1, 2019

(65) Prior Publication Data

US 2020/0061169 A1 Feb. 27, 2020

Related U.S. Application Data

(62) Division of application No. 14/758,319, filed as application No. PCT/US2014/010310 on Jan. 6, 2014, now Pat. No. 10,517,936.

(60) Provisional application No. 61/748,880, filed on Jan. 4, 2013.

(51) Int. Cl.
*A61K 39/00* (2006.01)
*C07H 15/24* (2006.01)
*A61K 39/39* (2006.01)

(52) U.S. Cl.
CPC ...... *A61K 39/001169* (2018.08); *A61K 39/39* (2013.01); *C07H 15/24* (2013.01); *A61K 2039/55577* (2013.01); *A61K 2039/6037* (2013.01); *A61K 2039/6081* (2013.01)

(58) Field of Classification Search
None
See application file for complete search history.

(56) References Cited

U.S. PATENT DOCUMENTS

| | | | |
|---|---|---|---|
| 5,057,540 | A | 10/1991 | Kensil et al. |
| 5,977,081 | A | 11/1999 | Marciani |
| 6,080,725 | A | 6/2000 | Marciani |
| 6,524,584 | B2 | 2/2003 | Kensil et al. |
| 6,544,952 | B1 | 4/2003 | Danishefsky et al. |
| 8,540,964 | B2 | 9/2013 | Livingston et al. |
| 9,028,836 | B2 | 5/2015 | Wong et al. |
| 2006/0035267 | A1 | 2/2006 | Livingston et al. |
| 2009/0317411 | A1 | 12/2009 | Wong et al. |
| 2010/0136042 | A1 | 6/2010 | Wong et al. |
| 2012/0328646 | A1 | 12/2012 | Wong et al. |

FOREIGN PATENT DOCUMENTS

| | | |
|---|---|---|
| CA | 2531023 | 1/2005 |
| CA | 2683681 | 10/2008 |
| CA | 2728341 | 1/2010 |
| CA | 2756053 | 1/2010 |
| CA | 2897272 | 8/2014 |
| CL | 2015001900 | 2/2016 |
| CN | 102215862 | 10/2011 |
| JP | 2002503705 | 2/2002 |
| WO | 1996040242 | 12/1996 |
| WO | 9942130 | 8/1999 |
| WO | 03/00514 | 1/2003 |
| WO | 2009126737 | 10/2009 |
| WO | 2011/156774 | 12/2011 |
| WO | 2011156774 | 12/2011 |
| WO | 2013142245 | 9/2013 |

OTHER PUBLICATIONS https://clinicaltrials.gov/ct2/history/NCT01516307?A=1&B=20&C=Side-by-Side, accessed Apr. 12, 2022, pp. 1-16.*

Pham et al (CDD, 3:389,397, 2006).*

Huang, Y.L, et al., "Carbohydrate-based vaccines: challenges and opportunities", Expert Reviews, 2010, pp. 1257-1274, vol. 9(11).

Kite, G.C., et al., "Metabolomic analysis of saponins in crude extracts of Quillaja saponaria by liquid chromatography/mass spectrometry for product authentication", Rapid Communications in Mass Spectrometry, Jul. 7, 2004 Revised and Accepted Oct. 2, 2004, vol. 18, pp. 2859-2870.

Chea, E.K., et al., "Synthesis and Preclinical Evaluation of QS-21 Variants Leading to Simplified Vaccine Adjuvants and Mechanistic Probes", Journal of the American Chemical Society, pp. 13448-13457.

Ragupathi, G., et al., "Natural and synthetic saponin adjuvant QS-21 for vaccines against cancer", NIH Public Access, Apr. 2011; 10(4): 463-470.

"Bivalent Vaccine with Escalating Doses of the Immunological Adjuvant OPT-821, in Combination with Oral β-glucan for I Neuroblastoma", NIH U.S. National Library of Medicine, Sep. 11, 2019, clinicaltrials.gov.

International Search Report and Written Opinion issued in corresponding International Application No. PCT/US14/10310 dated Oct. 31, 2014.

Huang, Y.L., et al., "Carbohydrate-based vaccines with a glycolipid adjuvant for breast cancer", Proceedings of the National Academy of Sciences, vol. 110, No. 7, Jan. 25, 2013, pp. 2517-2522.

(Continued)

*Primary Examiner* — Brad Duffy
(74) *Attorney, Agent, or Firm* — Michael Ye, Esq.; Rimon Law

(57) ABSTRACT

The present invention provides vaccines comprising carbohydrate antigen conjugated to a diphtheria toxin (DT) as a carrier protein, wherein the ratio of the number of carbohydrate antigen molecule to the carrier protein molecule is higher than 5:1. Also disclosed herein is a novel saponin adjuvant and methods to inhibit cancer cells, by administering an effective amount of the vaccine disclose herein.

5 Claims, 10 Drawing Sheets

(56) References Cited

OTHER PUBLICATIONS

Search Report and Written Opinion issued in Singapore Application No. 11201505301X.
Chong-Ya, L., "Review and outlook of the Pharmaceutical Industry in Taiwan in the 3rd Quarter, 2012", The World of Medicine Weekly, Nov. 26, 2011 (5 pages, including English Translation).
Optimer Pharmaceuticals, Inc. 2010 Annual Report.
Zhu, J., et al., "From Synthesis to Biologies: Pre-clinical Data on a Chemistry Derived Anticancer Vaccine", Journal of the American Chemical Society, vol. 131, No. 26, Jul. 8, pp. 9298-9303.
Huang, Y.L., et al., "Carbohydrate-based vaccines: challenges and opportunities", Expert Review of Vaccines, vol. 9, No. 11, Nov. 1, 2010, pp. 1257-1274.
Hong, et al., "The Known Immunologically Active Components of Astragalus Account for Only a Small Proportion of the Immunological Adjuvant Activity When Combined with Conjugate Vaccines", Planta Med, May 2011, vol. 77, No. 8, pp. 817-824.
Gilewski, et al., "Immunization of Metastic Breast Cancer Patients with a Fully Synthetic Globo H Conjugate: A Phase I Trail", Proceeding of National Academic of Science, Mar. 2011, vol. 98, No. 6, pp. 3270-3275.
Chuang, et al., "Synthesis and Vaccine Evaluation of the Tumor-Associated Carbohydrate Antigen RM2 from Prostate Cancer", Journal of the American Chemical Society, Jul. 2013, vol. 135, No. 30, pp. 11140-11150.
Yan, et al., "An Overview of the Research on the Use of Chinese Herbal Medicine as Vaccine Adjuvant", Chinese Journal of Veterinary Medicine, 2009(45) vol. 8, p. 61-63.
Kite, G., et al., "Metabolomic analysis of saponins in crude extracts Quillaja saponaria by liquid chromatography/mass spectrometry for product authentication", Rapid Communications in Mass Spectrometry, vol. 18, No. 23, Jan. 1, 2004 (Jan. 1, 2004), pp. 2859-2870.
Adams, M.M., et al., "Design and Synthesis of Potent Quillaja Saponin Vaccine Adjuvants", Journal of the American Chemical Society, vol. 132, No. 6, Feb. 17, 2010, pp. 1939-1945.
Ragupathi, G., et al., "Preclinical evaluation of the synthetic adjuvant SQS-21 and its constituent isomeric saponins", Vaccine, Elsevier, Amsterdam, NL, vol. 28, No. 26, (2010), pp. 4260-4267.
Ragupathi, G., et al., "Natural and synthetic saponin adjuvant QS-21 for vaccines against cancer", Expert Review of Vaccines, vol. 10, No. 4, Apr. 1, 2011, pp. 463-470.
Extended European Search Report issued in EP Application No. 20197437.7-1111, dated Feb. 15, 2021.
Liu, G., et al., "QS-21 structure/function studies: effect of acylation on adjuvant activity", Vaccine 20 (2002), pp. 2808-2815.
U.S. Appl. No. 16/671,395, filed Nov. 1, 2019, Pending.
Indian Examination Report for Indian Application No. 201918039840, dated Mar. 23, 2022.

* cited by examiner

ADCC raw data

ADCC normalized data

CDC raw data

CDC normalized data

- G1
- G2
- G3
- G4
- G5
- G6
- G7

Day 10 IgM

Day 17 IgM

Day 24 IgM

Day 10 IgG

Day 17 IgG

Day 24 IgG

VACCINES WITH HIGHER CARBOHYDRATE ANTIGEN DENSITY AND NOVEL SAPONIN ADJUVANT

This application is a Divisional of U.S. application Ser. No. 14/758,319, filed on Jun. 29, 2015, which is a National Stage Entry of PCT Application No. PCT/US2014/010310, filed on Jan. 6, 2014, which claims the benefit of U.S. Provisional Application No. 61/748,880, filed on 4 Jan. 2013, the entire disclosure of which is incorporated herein by reference.

BACKGROUND OF THE INVENTION

Cancer vaccines are designed to treat cancers by boosting the body's natural ability to protect itself, through the immune system. It has always represented a very attractive therapeutic approach, especially in light of the many shortcomings of conventional surgery, radiation and chemotherapies in the management of cancer. However, due to the low immunogenicity of the cancer carbohydrate antigen and the fact that many synthetic vaccines induce mainly IgM and to a lesser extent IgG antibody, the effectiveness of such cancer vaccine is still low. Various approaches have been explored, such as the use of an adjuvant, to aid immune recognition and activation.

There is an unmet need to develop a cancer vaccine and an effective adjuvant with improved immune response, especially IgG response. The present invention provides vaccines against carbohydrate antigens and adjuvant to satisfy these and other needs.

BRIEF SUMMARY OF THE INVENTION

In one embodiment, the present invention discloses a vaccine comprising a carbohydrate antigen or its immunogenic fragment; and a toxoid protein, wherein the ratio of carbohydrate antigen to toxoid protein ranges from 5:1 to 39:1, where the ratio represents the number of molecules of carbohydrate antigen to toxoid protein. It has been discovered that the IgG production of the vaccine with a carbohydrate antigen to toxoid protein ratio ranges from 5:1 to 39:1 is higher compare to that of a vaccine with a carbohydrate antigen to toxoid protein ratio equal to or less than 4:1.

One embodiment of the present invention provides for isolated compounds of formula (I)

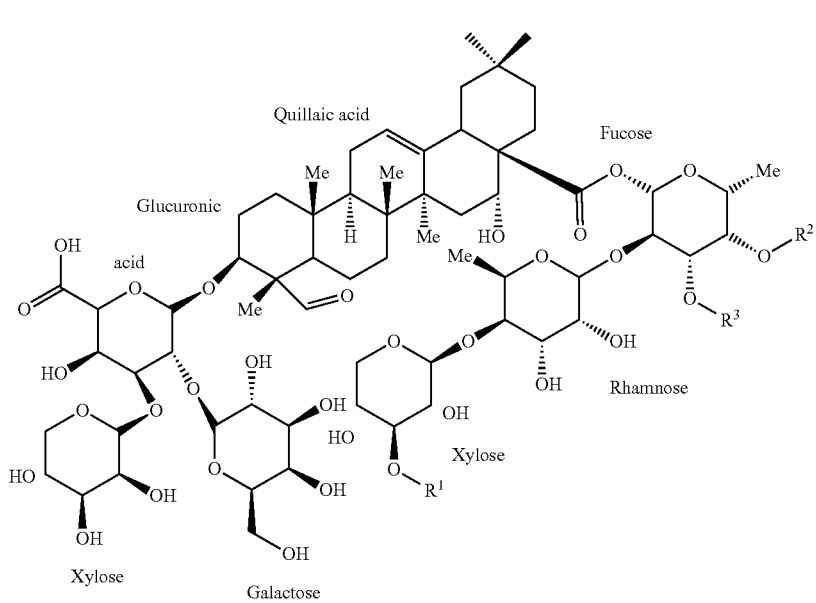

(I)

or a pharmaceutically acceptable salts thereof;
wherein
$R^1$ is selected from β-D-Apiose or β-D-Xylose;
$R^2$ and $R^3$ are selected from H, alkyl or

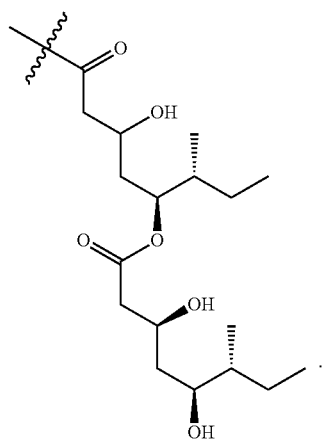 [SMILES: *C(=O)CC(O)C[C@H](OC(=O)C[C@@H](O)C[C@H](O)[C@H](C)CC)[C@H](C)CC]

Another embodiment of the present invention provides for pharmaceutical compositions comprising a compound of formula (I)

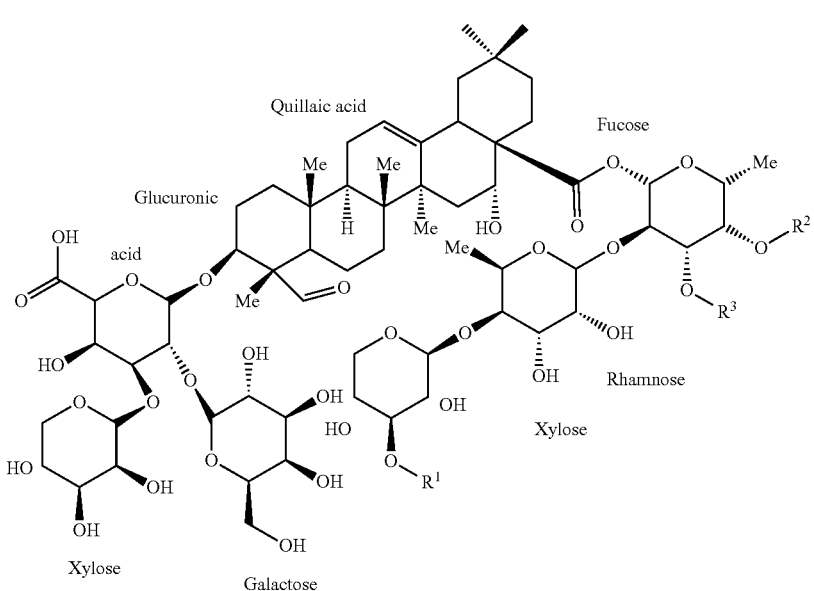

(I)

or a pharmaceutically acceptable salts thereof, wherein
R$^1$ is selected from β-D-Apiose or β-D-Xylose;
R$^2$ and R$^3$ are selected from H, alkyl or

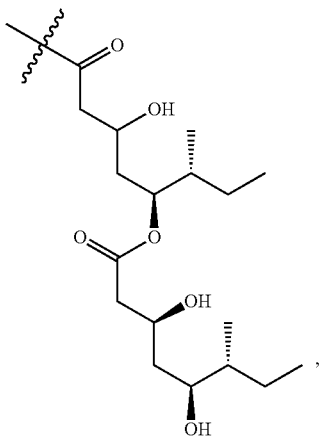 [SMILES: *C(=O)CC(O)C[C@H](OC(=O)C[C@@H](O)C[C@H](O)[C@H](C)CC)[C@H](C)CC]

and a pharmaceutically acceptable carrier.

A third embodiment of the present invention provides for a novel saponin adjuvant, OBI-821, which comprises 1857 compound V1A, 1857 compound V1B, 1857 compound V2A and 1857 compound V2B.

A fourth embodiment of the present invention provides for vaccines comprising a carbohydrate antigen or its immunogenic fragment; and OBI-821 saponin adjuvant. In one embodiment, the vaccine further comprises a carrier protein. It has been discovered that the IgG production, antibody-dependent cell-mediated cytotoxicity (ADCC) and/or complement-dependent cytotoxicity (CDC) activities of the vaccine with OBI-821 saponin adjuvant are higher compare to that of a vaccine without the OBI-821 saponin adjuvant.

The present invention is also directed to methods for (i) inhibiting cancer cells, comprising administering an effective amount of the vaccine described herein, wherein the cancer cells are inhibited; and, (ii) inducing an immune response, comprising administering an effective amount of the vaccine described herein to a subject in need thereof.

The present invention also discloses a pharmaceutical composition comprising the vaccine described herein and a pharmaceutically acceptable excipient or carrier.

Statements containing these terms should be understood not to limit the subject matter described herein or to limit the meaning or scope of the patent claims below. Embodiments of the invention covered by this patent are defined by the claims below, not this summary. This summary is a high-level overview of various aspects of the invention and introduces some of the concepts that are further described in the Detailed Description section below. This summary is not intended to identify key or essential features of the claimed subject matter, nor is it intended to be used in isolation to determine the scope of the claimed subject matter. The subject matter should be understood by reference to appropriate portions of the entire specification, any or all drawings and each claim.

The invention will become more apparent when read with the accompanying figures and detailed description which follow.

BRIEF DESCRIPTION OF THE DRAWINGS

Illustrative embodiments of the present invention are described in detail below with reference to the following Figures:

FIG. 2A illustrates the ADCD raw data, FIG.

2B illustrates the ADCD normalized data, FIG. 2C illustrates the CDC raw data and FIG. 2D illustrates the CDC normalized data.

DETAILED DESCRIPTION OF THE INVENTION

Figure 1A:
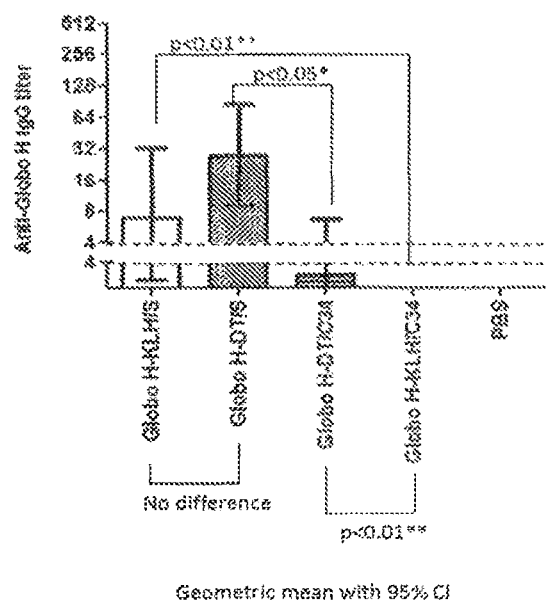
FIG. 1A is a bar graph illustrating quantitative Anti-Globo H IgG titer on Day 24 for the following compositions: Globo H/KLH/OBI-821 saponin, Globo H/DT/OBI-821 saponin, Globo H/DT/C34 and Globo H/KLH/C34.

In order to provide a clear and ready understanding of the present invention, certain terms are defined herein. Unless defined otherwise, all technical and scientific terms used herein have the same meanings as is commonly understood by one of skill in the art to which this invention belongs.

An "effective amount," as used herein, refers to a dose of the vaccine or pharmaceutical composition that is sufficient to reduce the symptoms and signs of cancer, which include, but are not limited to, weight loss, pain and tumor mass, which is detectable, either clinically as a palpable mass or radiologically through various imaging means.

The term "subject" can refer to a vertebrate having cancer or to a vertebrate deemed to be in need of cancer treatment. Subjects include warm-blooded animals, such as mammals, such as a primate, and, more preferably, a human. Non-human primates are subjects as well. The term subject includes domesticated animals, such as cats, dogs, etc., livestock (for example, cattle, horses, pigs, sheep, goats, etc.) and laboratory animals (for example, mouse, rabbit, rat, gerbil, guinea pig, etc.). Thus, veterinary uses and medical formulations are contemplated herein.

As used herein, the term "alkyl" refers to a straight or branched monovalent hydrocarbon containing, unless otherwise stated, 1-20 carbon atoms, e.g., $C_1$-$C_8$ or $C_1$-$C_4$, which can either be substituted or unsubstituted (other chain lengths, e.g., 21-30, may be encompassed by the invention). Examples of alkyl include, but are not limited to, methyl, ethyl, n-propyl, i-propyl, n-butyl, i-butyl, and t-butyl.

The term "substantially pure" means substantially free from compounds normally associated with the saponin in its natural state and exhibiting constant and reproducible chromatographic response, elution profiles, and biologic activity. The term "substantially pure" is not meant to exclude artificial or synthetic mixtures of the saponin with other compounds.

All numbers herein may be understood as modified by "about."

Vaccines with Higher Carbohydrate Ratio

Tumor associated carbohydrate antigens generally exhibit poor immunogenicity. A carbohydrate antigen conjugated with a carrier protein has been adopted to increase the immunogenicity of said carbohydrate antigen. For example, about 700 Globo H molecules are conjugated to one non-toxic keyhole limpet hemocyanin (KLH) protein, an average of about 2 to 4 Globo H molecules are conjugated to diphtheria toxin (DT), about 8 Globo H molecules are conjugated to bovine serum albumin (BSA), and about 6 Globo H molecules are conjugated to Tetanus Toxoid (Table 1 of U.S. Pat. No. 8,268,969).

The present invention provides for a vaccine comprising a carbohydrate antigen or its immunogenic fragment; and a toxoid protein, wherein the ratio of carbohydrate antigen to toxoid protein ranges from 5:1 to 39:1, and the ratio reflects the number of molecules of carbohydrate antigen or its immunogenic fragment to molecules of toxoid protein. Such vaccine exhibits a better immunogenicity compare to a vaccine with a carbohydrate antigen molecule to toxoid protein molecule ratio equal to or less than 4:1. Other ranges are also encompassed by the invention, including ratios of number of molecules of carbohydrate antigen or its immunogenic fragment to molecules of toxoid protein of 4:1, 5:1, 6:1, 7:1, 8:1, 9:1, 10:1, 11:1, 12:1, 13:1, 14:1, 15:1, 16:1, 17:1, 18:1, 19:1, 20:1, 21:1, 22:1, 23:1, 24:1, 25:1, 26:1, 27:1, 28:1, 29:1, 30:1, 31:1, 32:1, 33:1, 34:1, 35:1, 36:1, 37:1, 38:1 or 39:1.

In one embodiment, the toxoid protein is tetanus toxoid (TT) and the ratio of carbohydrate antigen to TT in the carbohydrate-TT vaccine ranges from 7:1 to 12:1.

The present invention provides for a vaccine comprising a carbohydrate antigen or its immunogenic fragment; and a diphtheria toxin (DT), wherein the ratio of carbohydrate antigen to DT ranges from 5:1 to 39:1, where the ratio reflects the number of molecules of carbohydrate antigen or its immunogenic fragment to molecules of DT. In another embodiment, the ratio of carbohydrate antigen to DT in the carbohydrate-DT vaccine ranges from 8:1 to 24:1.

Examples of carbohydrate antigens include, but are not limited to Globo H, stage-specific embryonic antigen 3 (SSEA3) (also called Gb5), stage-specific embryonic antigen 4 (SSEA-4), Gb-4, Gb-3, Lewis antigens such as sLe$^x$, Le$^x$, sLe$^a$, Le$^a$, Le$^y$, polysaccharide antigens such as polysialic acid (PSA), sTn(c), Tn(c), Thomsen-Friedenreich antigen (TF(c)), the ganglioside such as GD1, GD2, GD3, Fucosyl, GM1, GM1, GM2, GM3, GD1α and GM2. Other carbohydrate antigens include, but are not limited to: α-Galactose, α-Man-6-phosphate, α-L-Rhamnose, α-GalNAc (Tn), α-NeuAc-OCH2C6H4-p-NHCOOCH2, Fucα1-2Galβ1-4GalNAcβ (H types3), NeuAcα2-8NeuAcα, (NeuAcα2-8)2 Polysialic acid, NeuAca2-6Galb, NeuAcb2-6Gala(STn), Gala1-3Galb1-4GlaNAcb (NeuAca2-8)3, GalNAcαa-3(Fucα1-2)Galβ (Blood Group A), Galα1-3 (Fucα1-2)Galβ (Blood Group B), 6Gal-HSO3-SiaLex, 6GluNAc-HSO3-SiaLex and α 2-6 sialylated diantennary N-glycans. In one embodiment, the carbohydrate antigen is Globo H. "Globo H" is a hexasaccharide (Fucα1→2Galβ1→3GalNAcβ1→3Galα1→4Galβ1→4Glcβ1) which was originally isolated from the human breast cancer cell line MCF-7 (Menard S, Tagliabue E, Canevari S, Fossati G, Colnaghi M I. (1983) Generation of monoclonal antibodies reacting with normal and cancer cells of human breast. Cancer Res, 43, 1295-300; and Bremer E G, Levery S B, Sonnino S, Ghidoni R, Canevari S, Kannagi R, Hakomori S. (1984) Characterization of a glycosphingolipid antigen defined by the monoclonal antibody MBr1 expressed in normal and neoplastic epithelial cells of human mammary gland. *J Biol Chem*, 259, 14773-7). Globo H is expressed in a variety of epithelial cell tumors such as colon, ovarian, gastric, pancreatic, endometrial, lung, prostate and breast cancers (Menard S et al. supra; Bremer E G et al., supra; Canevari S, Fossati G, Balsari A, Sonnino S, Colnaghi M I. (1983). Globo H is commercially available (for example, Carbosynth, UK) and can be synthesized by attaching glycoside to ceramide using methods well known in the art.

The vaccine with a carbohydrate antigen to toxoid protein ratio greater than or equal to 5:1 are manufactured in a basic condition, i.e. at a pH over or equal to 8, over or equal to 9, over or equal to 10, over or equal to 11, or over or equal to 12. The ratio of carbohydrate antigen to toxoid protein can be determined by methods known in the art, for example, MALDI-TOF Mass Spectrometry. U.S. Pat. No. 8,268,969; see also, Morelle W, Faid V, Chirat F, Michalski J C. *Methods Mol Biol.* 2009; 534:5-21. doi: 10.1007/978-1-59745-022-5_1. Analysis of N- and O-linked glycans from glycoproteins using MALDI-TOF mass spectrometry.

The vaccine may further comprise an adjuvant, where the adjuvant is a saponin, such as OBI-821, which is described herein or synthetic analogs of α-Galactosyl-ceramide (α-GalCer or C1).

The terms "α-galactosyl-ceramide" and "α-GalCer" refer to a glycolipid that stimulates natural killer T cells to produce both T helper (TH)1 and TH2 cytokine, as described in U.S. Pat. No. 8,268,969, the content of which is incorporate by reference in its entirety. In one embodiment, α-GalCer adjuvant has the following structure:

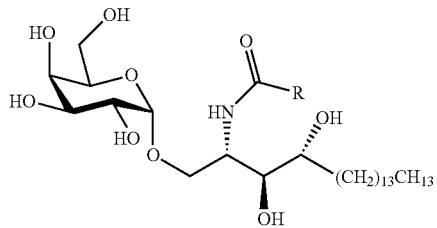

wherein R is $(CH_2)_{24}CH_3$, $(CH_2)_7PhF$, $(CH_2)_{10}PhOPhF$ or $(CH_2)_{10}PhF$.

In one embodiment, R is $(CH_2)_{10}PhOPhF$, known as C34 adjuvant with the following structure:

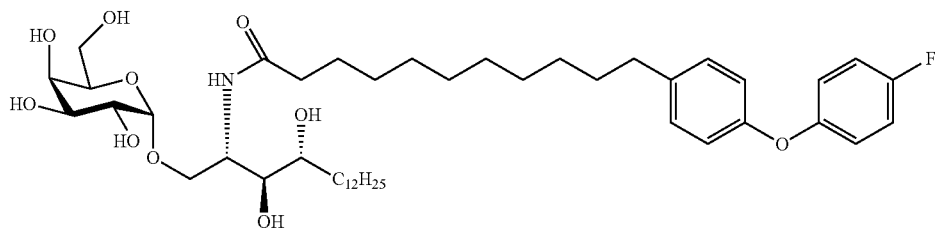

Novel Saponin Adjuvant

The present invention provides for OBI-821 saponins which can be substantially pure. The invention encompasses both OBI-821 saponin which are substantially pure as well as biologically active fragments. The invention may also encompass impure forms of OBI-821 saponins. The purified OBI-821 saponins exhibit enhanced adjuvant effect when administered with a vaccine described herein or admixed with other substantially pure saponin or non-saponin adjuvants.

OBI-821 saponins are naturally occurring glycosides, extracted in high purify from the bark of the *Quillaja saponaria* Molina tree, by high pressure liquid chromatography (HPLC), low pressure liquid silica chromatography, and hydrophilic interactive chromatography (HILIC) as described in, for example, U.S. Pat. Nos. 5,057,540 and 6,524,584, the content of which is incorporate by reference in its entirety. High-pressure liquid chromatography analysis shows that OBI-821 are a mixture of structurally related isomeric compounds. Different purified isomeric compounds of OBI-821 saponins have been identified and disclosed herein.

OBI-821 saponin comprise at least one isolated compound of formula I as follows:

Formula (I)

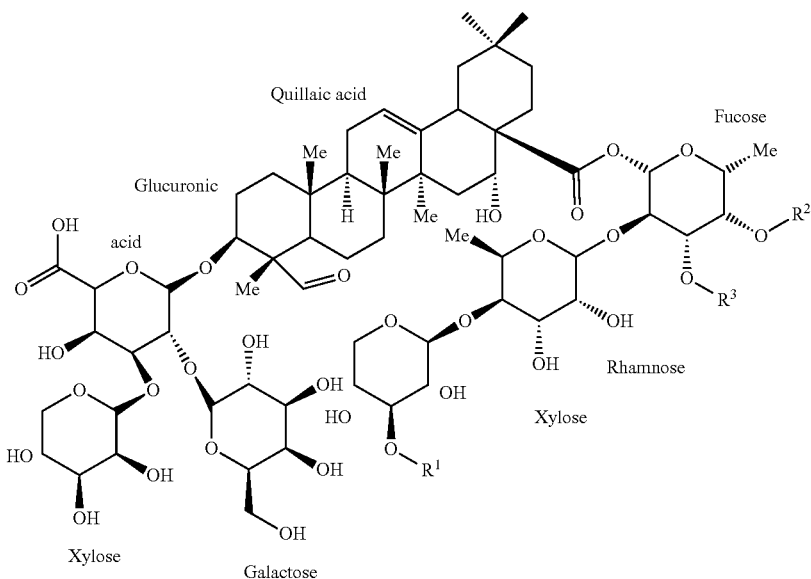

wherein

R[1] is β-D-Apiose or β-D-Xylose; and

R[2] and R[3] are independently H, alkyl,

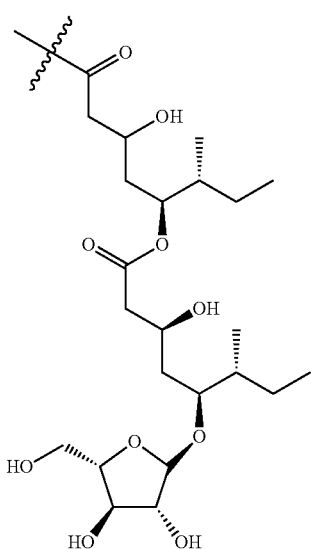

(Fatty acyl moiety for the 1989 Compound), or

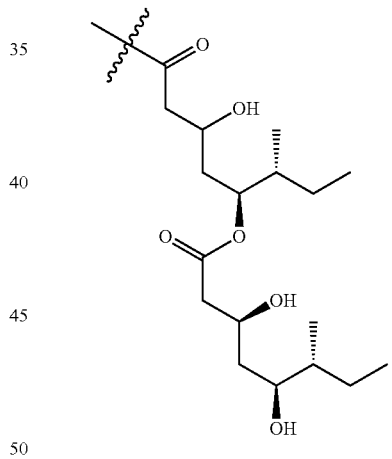

(Fatty acyl moiety for the 1857 Compound).

OBI-821 saponin can also comprise an isolated compound of formula I wherein (i) R[1] is β-D-Apiose, R[2] is the fatty acyl moiety for the 1989 compound depicted above, and R[3] is H (1989 compound V1A); (ii) R[1] is β-D-Apiose, R[2] is H, and R[3] is the fatty acyl moiety fatty acyl moiety for the 1989 compound depicted above (1989 compound V1B); (iii) R[1] is β-D-Xylose, R[2] is the fatty acyl moiety fatty acyl moiety for the 1989 compound depicted above, and R[3] is H (1989 compound V2A); or (iv) R[1] is β-D-Xylose, R[2] is H, and R[3] is the fatty acyl moiety fatty acyl moiety for the 1989 compound depicted above (1989 compound V2B). Collectively, 1989 compound V1A, 1989 compound V1B, 1989 compound V2A and 1989 compound V2B are called "1989 compounds mixture."

Table 1 summarizes the functional groups of 1989 compounds and the mole % of each 1989 compound in the 1989 compounds mixture.

TABLE 1

| Mole % | R$^1$ | R$^2$ | R$^3$ |
|---|---|---|---|
| 1989 Compound V1A 64.5% | β-D-Apiose | [structure] | H |
| 1989 Compound V1B 1.5% | β-D-Apiose | H | [structure] |

TABLE 1-continued

| Mole % | R¹ | R² | R³ |
|---|---|---|---|
| 1989 Compound V2A 33.3% | β-D-Xylose | (fatty acyl moiety structure) | H |
| 1989 Compound V2B 0.7% | β-D-Xylose | H | (fatty acyl moiety structure) |

OBI-821 saponin can comprise an isolated compound of formula I where: (i) $R^1$ is β-D-Apiose, $R^2$ is the fatty acyl moiety for the 1857 compound depicted above, and $R^3$ is H (1857 compound V1A); (ii) $R^1$ is β-D-Apiose, $R^2$ is H, and $R^3$ is the fatty acyl moiety for the 1857 compound depicted above (1857 compound V1B); (iii) $R^1$ is β-D-Xylose, $R^2$ is the fatty acyl moiety for the 1857 compound depicted above, and $R^3$ is H (1857 compound V2A); or, (iv) $R^1$ is β-D-Xylose, $R^2$ is H, and $R^3$ is the fatty acyl moiety for the 1857 compound depicted above (1857 compound V2B). Collectively, 1857 compound V1A, 1857 compound V1B, 1857 compound V2A and 1857 compound V2B are called "1857 compounds mixture."

Table 2 summarizes the functional groups of 1857 compounds and the mole % of each 1857 compound in the 1857 compounds mixture.

TABLE 2

| Mole % | R¹ | R² | R³ |
|---|---|---|---|
| 1857 Compound V1A 64.7% | β-D-Apiose | (structure) | H |
| 1857 Compound V1B 1.3% | β-D-Apiose | H | (structure) |
| 1857 Compound V2A 33.4% | β-D-Xylose | (structure) | H |

TABLE 2-continued

| Mole % | R$^1$ | R$^2$ | R$^3$ |
|---|---|---|---|
| 1857 Compound V2B 0.6% | β-D-Xylose | H | |

OBI-821 saponin comprises one or more of the following compounds: (i) 1857 compound V1A; (ii) 1857 compound V1B; (iii) 1857 compound V2A; (iii) 1857 compound V2B; (iv) 1989 compound V1A; (v) 1989 compound V1B; (vi) 1989 compound V2A; or (vii) 1989 compound V2B. The percentages of the 1857 compounds mixture and the 1989 compound mixture in OBI-821 saponin can range as follows:

(i) about 1 mole % to about 15 mole % of OBI-821 comprising an 1857 compounds mixture; and
(ii) about 85 mole % to about 99 mole % of OBI-821 comprising an 1989 compounds mixture.

All of the mole % can be varied by 0.1% increment (e.g. about 87% to about 90%, about 90.5% to about 97%, about 3.5% to about 11%, about 10% to about 14%).

The 1989 compounds mixture may comprise about 60-70 mole % of 1989 compound V1A; about 1-5 mole % of 1989 compound V1B; about 30-40 mole % of 1989 compound V2A; and, about 0.1-3 mole % of 1989 compound V2B. All of the mole % can be varied by 0.1 increment (e.g. 65%, 2.5%, 35.6%).

The 1857 compounds mixture may comprise about 60-70 mole % of 1857 compound V1A; about 1-5 mole % of 1857 compound V1B; about 30-40 mole % of 1857 compound V2A; and, about 0.1-3 mole % of 1857 compound V2B. All of the mole % can be varied by 0.1 increment (e.g. 67%, 1.5%, 33.9%).

In another embodiment, the substantially pure OBI-821 is purified from a crude *Quillaja saponaria* extract, wherein said OBI-821 is characterized by a single predominant peak which comprises 90% or more of the total area of all peaks of a chromatogram, excluding the solvent peak, when analyzed on reverse phase-HPLC on a Symmetry C18 column having 5 um particle size, 100 Å pore, 4.6 mm ID×25 cm L with a elution program comprising mobile phase of A:B 95%:5% to 75%:25% in 11 minutes, which mobile phase A is distilled water with 0.1% trifluoroacetic acid, and mobile phase B is acetonitrile with 0.1% trifluoroacetic acid at a flow rate of 1 ml/min.

In one embodiment, the pharmaceutical composition comprises the compound of formula (I)

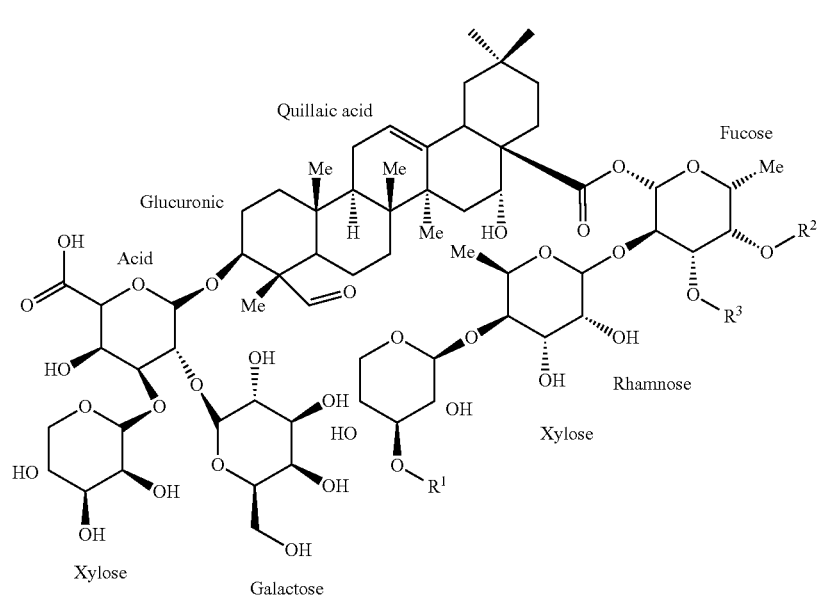

Formula (I)

wherein,
R¹ is β-D-Apiose or β-D-Xylose; and
R² and R³ are independently H, alkyl, or

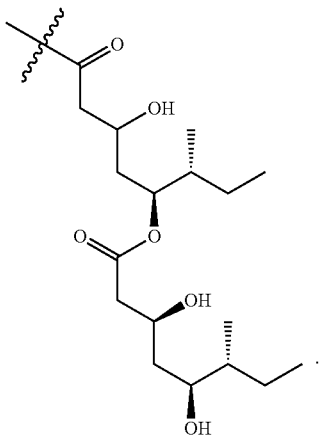 [SMILES: *C(=O)CC(O)C[C@H](OC(=O)C[C@@H](O)C[C@H](O)[C@H](C)CC)[C@H](C)CC]

(Fatty acyl moiety for the 1857 Compound),
and a pharmaceutically acceptable carrier.

The vaccine can comprise a carbohydrate antigen or its immunogenic fragment and an OBI-821 saponin. In another embodiment, the vaccine comprises a carbohydrate antigen selected from Globo H, SSEA-3, SSEA-4, Gb-4 or a mixture thereof, a DT, and an OBI-821 saponin. In yet another embodiment, the vaccine comprises a carbohydrate antigen or its immunogenic fragment; a carrier protein and an OBI-821 saponin. Non limiting examples of carrier protein include toxoid proteins and non-toxoid protein such as KLH.

Toxoid Protein

The toxoid protein conjugated to carbohydrate antigen may be a diphtheria toxins (DT) or tetanus toxoids (TT).

Toxins can be inactivated, for example, by treatment with formaldehyde, glutaraldehyde, UDP-dialdehyde, peroxide, oxygen or by mutation (e.g., using recombinant methods). Relyveld et al., Methods in Enzymology, 93:24, 1983. Woodrow and Levine, eds., New Generation Vaccines, Marcel Dekker, Inc., New York, 1989. Genth et al., Inf. and Immun., 68(3):1094-1101, 2000. Mutant diphtheria toxins with reduced toxicity can also be produced using recombinant methods. U.S. Pat. Nos. 5,085,862; 5,221,618; 5,244,657; 5,332,583; 5,358,868; and 5,433,945.

DT is diphtheria toxin cross-reacting materials (DT-CRM) or diphtheria toxoids. An DT-CRM refers to a mutant diphtheria toxin, e.g., by mutation or by chemical modification, such that it no longer possesses sufficient ADP-ribosyl. Non limiting examples of DT-CRM include DT-CRM 30, DT-CRM 45, DT-CRM 176, DT-CRM 197 and DT-CRM 228. A diphtheria toxoid is a formaldehyde-inactivated diphtheria toxin. DT is commercially available from or can be prepared by methods known in the art, such as recombinant DNA technology as described in U.S. Pat. No. 5,614,382, the content of which is incorporated by reference in its entirety.

The carbohydrate antigen of the vaccine described herein may be covalently bonded to a carrier protein, via a p-nitrophenyl linker by a synthetic process described in U.S. Pat. No. 8,268,969, the content of which is incorporate by reference in its entirety.

The vaccines of the present invention can induce one or more of the following activities: a higher IgG titer as compare to IgM titer, a higher complement-dependent cytotoxicity (CDC) activity, and/or a higher antibody-dependent cell-mediated cytotoxicity (ADCC) activity. In another embodiment, the vaccines induce one or more of the following cells: natural killer cells, CD4+ T lymphocytes or CD8+ T lymphocytes. Other immunological parameters may be measured, including, but not limited to, T helper cell activation.

The invention also provides a pharmaceutical composition comprising the vaccines described herein and a pharmaceutically acceptable vehicle, excipient or carrier. Suitable vehicles are, for example, water, saline, dextrose, glycerol, ethanol, or the like, and combinations thereof. In addition, the vehicle can contain other excipients, such as wetting or emulsifying agents, pH buffering agents, or adjuvants. Pharmaceutically acceptable carriers can contain a physiologically acceptable compound that acts to, e.g., stabilize, or increase or decrease the absorption or clearance rates of the pharmaceutical compositions of the invention. Physiologically acceptable compounds can include, e.g., carbohydrates, such as glucose, sucrose, or dextrans, antioxidants, such as ascorbic acid or glutathione, chelating agents, low molecular weight proteins, detergents, liposomal carriers, or other stabilizers and/or buffers. The excipients may be nonionic surfactants, polyvinylpyrollidone, human serum albumin, aluminum hydroxide, agents with anesthetic action, and various unmodified and derivatized cyclodextrins. More preferably, the nonionic surfactants may include Polysorbate 20, Polysorbate 40, Polysorbate 60, and Polysorbate 80. The polyvinylpyrollidone may preferably be Plasdone C15, a pharmaceutical grade of polyvinylpyrollidone. The agent having anesthetic action preferably is benzyl alcohol. Other physiologically acceptable compounds include wetting agents, emulsifying agents, dispersing agents or preservatives. See e.g., the 21st edition of Remington's Pharmaceutical Science, Mack Publishing Company, Easton, Pa. ("Remington's"). The pharmaceutical compositions of the present invention can also include ancillary substances, such as pharmacological agents, cytokines, or other biological response modifiers. The pharmaceutical composition comprising such excipient or carrier are formulated by well-known conventional methods.

The vaccine may be formulated for the following route of administration: intramuscular, intradermal, oral, dermal, nasal, buccal, rectal, vaginal, by inhalation, or by subcutaneous administration. Other modes of administration may be applicable as long as a satisfactory immunogenicity can be induced.

The pharmaceutical compositions of the present invention can be prepared as injectables, either as liquid solutions or suspensions, or as solid forms which are suitable for solution or suspension in liquid vehicles prior to injection. The pharmaceutical composition can also be prepared in solid form, emulsified or the active ingredient encapsulated in liposome vehicles or other particulate carriers used for sustained delivery. For example, the pharmaceutical composition can be in the form of an oil emulsion, water-in-oil emulsion, water-in-oil-in-water emulsion, site-specific emulsion, long-residence emulsion, stickyemulsion, microemulsion, nanoemulsion, liposome, microparticle, microsphere, nanosphere, nanoparticle and various natural or synthetic polymers, such as nonresorbable impermeable polymers such as ethylenevinyl acetate copolymers and Hytrel® copolymers, swellable polymers such as hydrogels, or resorbable polymers such as collagen and certain polyacids or polyesters such as those used to make resorbable sutures, that allow for sustained release of the vaccine.

Pharmaceutically acceptable salts of the compounds of the invention and physiologically functional derivatives thereof include salts derived from an appropriate base, such as an alkali metal (for example, sodium, potassium), an alkaline earth metal (for example, calcium, magnesium), ammonium and $NX_4^+$ (wherein X is $C_1$-$C_4$ alkyl). Pharmaceutically acceptable salts of an amino group include salts of organic carboxylic acids, such as tartaric, aliphatic, cycloaliphatic, aromatic, heterocyclic, carboxylic and sulfonic classes of organic acids, such as, for example, formic, glucuronic, malic, maleic, fumaric, pyruvic, aspartic, glutamic, benzoic, anthranilic, mesylic, salicylic, hydroxybenzoic, phenylacetic, mandelic, embonic (pamoic), methanesulfonic, ethanesulfonic, benzenesulfonic, pantothenic, toluenesulfonic, 2-hydroxyethanesulfonic, sulfanilic, stearic, algenic, hydroxybutyric, cyclochexylaminosulfonic, galactaric and galacturonic acid and the like, lactobionic, fumaric, and succinic acids; organic sulfonic acids, such as methaniesulfolic, ethanesulfonic, isothionic, benzenylesulfonic and p-toluenesulfonic acids; and inorganic acids such as hydrochloric, hydrobromic, hydroiodic, nitric, carbonic, sulfuric, sulfamic and phosphoric acid and the like. Pharmaceutically acceptable salts of a compound having a hydroxy group consist of the anion of said compound in combination with a suitable cation such as $Na^+$, $NH_4^+$ or $NX_4^+$ (wherein X is, for example, a $C_1$-$C_4$ alkyl group), $Ca^{++}$, $Li^{++}$, $Mg^{++}$, or, $K^+$ and zinc or organic salts made from primary, secondary and tertiary amines, cyclic amines, N,N'-dibenzylethylenediamine, chloroprocaine, choline, diethanolamine, ethylenediamine, meglumine (N-methylglucamine) and procaine and the like. All of these salts may be prepared by conventional means from the corresponding compound by reacting, for example, the appropriate acid or base with the compound in free form.

Methods for Inducing Immune Response/Inhibiting Cancer Cells

Another aspect of the present invention directed to methods for inducing immune response comprising administering an effective amount of the vaccine described herein to a subject in need thereof. The immune response includes but is not limited to, NK cell response, ADCC and CDC activity, and IgM and IgG production.

In yet another aspect, the present invention provides methods for inhibiting cancer cells, comprising administering an effective amount of the vaccine described herein to a subject in need thereof. In one embodiment, the cancer is selected from breast cancer, lung cancer, esophageal cancer, rectal cancer, biliary cancer, liver cancer, buccal cancer, gastric cancer, colon cancer, nasopharyngeal cancer, kidney/renal cancer, brain tumor, prostate cancer, ovarian cancer, cervical cancer, endometrial cancer, pancreatic cancer, testicular cancer, bladder cancer, head and neck cancer, oral cancer, neuroendocrine cancer, adrenal cancer, thyroid cancer, bone cancer, skin cancer (e.g. basal cell carcinoma, squamous cell carcinoma or melanoma). In another embodiment, the cancer is a Globo H expressing cancer. Non limiting examples of Globo H expressing cancer include breast cancer, lung cancer gastric cancer, colon cancer, pancreatic cancer, prostate cancer, ovarian cancer and endometrial cancer. The antibody generated by the vaccine, such as anti-Globo H antibody, inherently inhibits Globo H expressing cancer.

In certain embodiments, the effective amount of a vaccine is to induce desired immunological effects, such as stimulating IgG production against a specific carbohydrate antigen (e.g. Globo H) in a subject. The effective amount or dose of a vaccine or a pharmaceutical composition may vary depending on the amount of carbohydrate antigen, the type of adjuvant employed, the mode of administration, and the age, size, and condition of the subject to be treated. Precise amount of the vaccine or pharmaceutical composition required to induce immunogenicity will be determined by the medical practitioner.

The vaccine can be administered as a stat dose with or without one or more booster dose at a specific time intervals, to achieve a long term immune protective effect between several months to several years. The frequency of administration can vary depending on any of a variety of factors, e.g., severity of the symptoms, degree of immunoprotection desired, whether the pharmaceutical composition is used for prophylactic or curative purposes, etc. For example, in one embodiment, the pharmaceutical composition according to the invention is administered once per month, twice per month, three times per month, every other week (qow), once per week (qw), twice per week (biw), three times per week (tiw), four times per week, five times per week, six times per week, every other day (qod), daily (qd), twice a day (qid), or three times a day (tid). The vaccine can also be administered with other conventional therapy such as chemotherapy, targeted therapy or antibodies targeting the tumor associated carbohydrate antigen for cancer treatment, either simultaneously or sequentially.

The present invention is further illustrated by the following examples, which are provided for the purpose of demonstration rather than limitation. Those of skill in the art should, in light of the present disclosure, appreciate that many changes can be made in the specific embodiments which are disclosed and still obtain a like or similar result without departing from the spirit and scope of the invention.

Example 1: Preparation of a Vaccine with a Higher Carbohydrate/Toxin Protein Ratio and Extraction of OBI-821

Globo H was conjugated with KLH or DT, according to methods known in the art, for example, as described in U.S. Pat. No. 6,544,952 or 8,268,969, the content of which are hereby incorporated by reference in its entirety. The resultant vaccine comprised Globo H:DT (ratio of molecules of Globo H to DT=2-4:1)

General Procedure for Generating Glycoconjugates
Glycoconjugates were manufactured as follows:

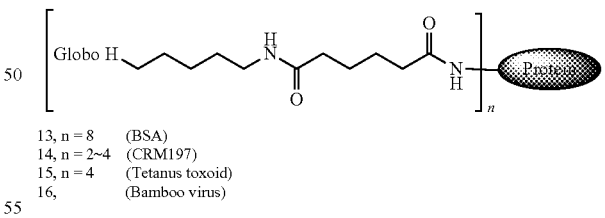

13, n = 8   (BSA)
14, n = 2~4 (CRM197)
15, n = 4   (Tetanus toxoid)
16,         (Bamboo virus)

BSA, DT-CRM197, and Tetanus toxoid (Adimmune, Taiwan) was dissolved in 100 mM phosphate buffer pH 7.2 (5 mg/ml), and 30 to 40 equivalents of Globo H half ester 35 were added to the solution. The mixture was stirred gently for 24 h at room temperature. The mixture was then diluted with deionized water and dialyzed against 5 changes of deionized water. The solution was then lyphophilized to a white powder. The obtained Globo H-protein conjugates can be characterized by MALDI-TOF analysis to determine the carbohydrate incorporation rate. 41 (GH-BSA), MALDI-TOF found 76029, 42 (GH-DT-CRM197) found 62138, 43

(GH-TT) found 162902, 44 (GH-BaMV) was not determined. MALDI-TOF MS Analysis for Glycoconjugates. The glycoconjugates and primary carrier proteins can be reconstituted with ddH$_2$O (~1 μg/μl). The matrix, sinapinic acid, was freshly prepared with acetonitrile and deionized water 1:1, making final matrix concentration in 10 mg/ml including 0.1% TFA. Gently loaded and mixed the matrix solution and glycoconjugates, then air dried the plate. Calibration was imperative using bovine serum albumin before measurement. Each glycoconjugate and primary protein sample was detected under linear positive mode. The average molecular weight allows the calculation of the average number of carbohydrate molecules incorporated on the carrier protein.

A vaccine with carbohydrate antigen molecule:toxin protein molecule ratio over 5:1 was manufactured according to the following steps:
(a) 10 ml-25 ml of Globo H (available from OBI Pharma, Taiwan) and p-nitrophenyl ester linker (available from OBI Pharma, Taiwan) was dissolved in 25 μl DMF (commercially available from Sigma-Aldrich, USA).
(b) 25 mg of DT was dissolved with 2.5 ml of phosphate buffer (i.e. a basic buffer with pH>8).
(c) The mixture in step (a) was added to mixture in step (g) at room temperature overnight. The resultant mixture had a pH between 8 to 9.2

Results: 10 ml of Globo H resulted in vaccines comprising Globo H:DT (8:1) and 25 of Globo H resulted in vaccines comprising Globo H:DT (24:1), as determined by MALDI-TOF MS.

Figure 5A:
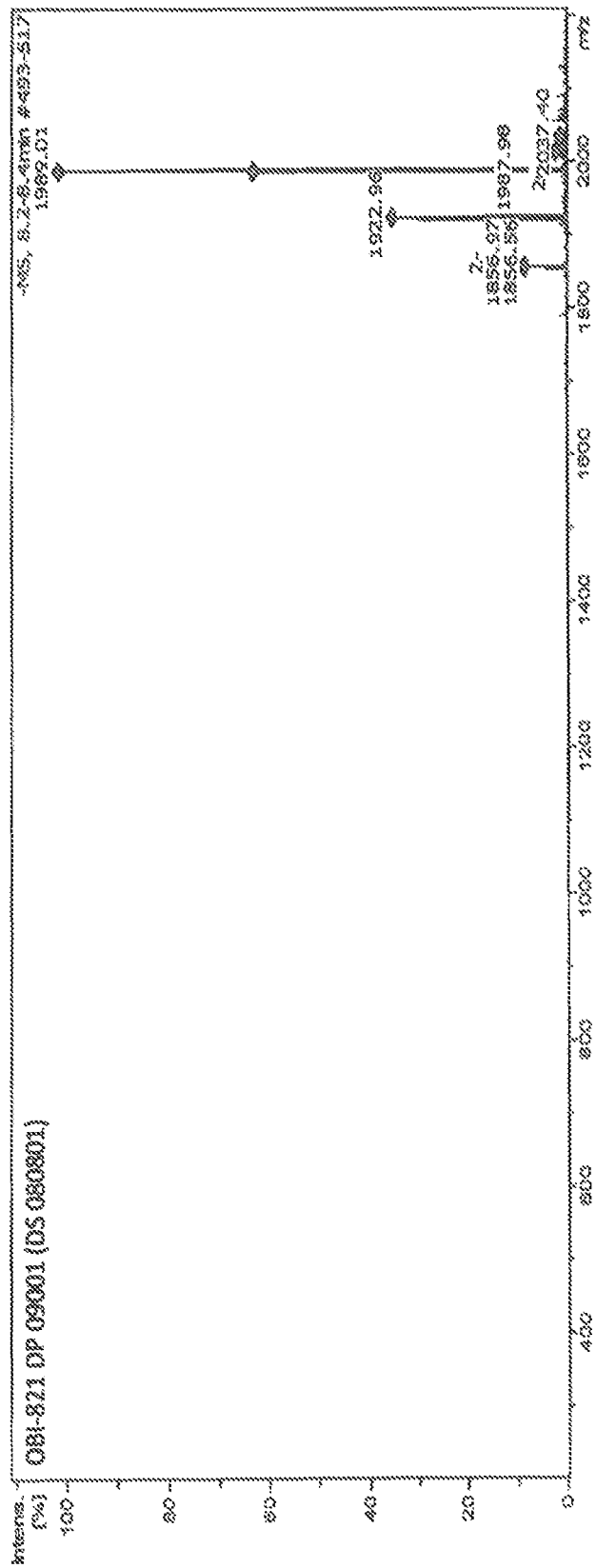
FIG. 5A-FIG. 5C are mass spectrum images of OBI-821 (comprising compounds 1989 and 1857).
Figure 5B:
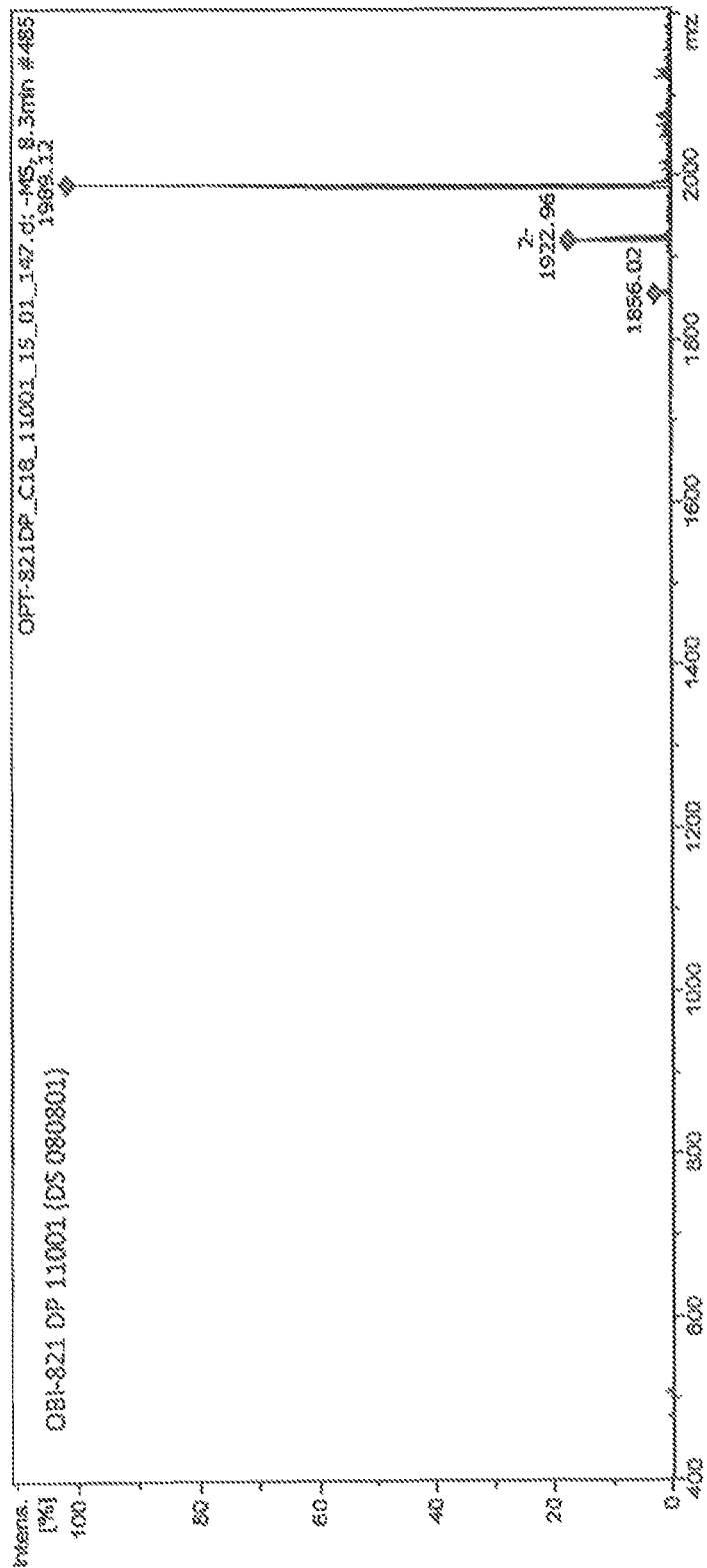
Figure 5C:
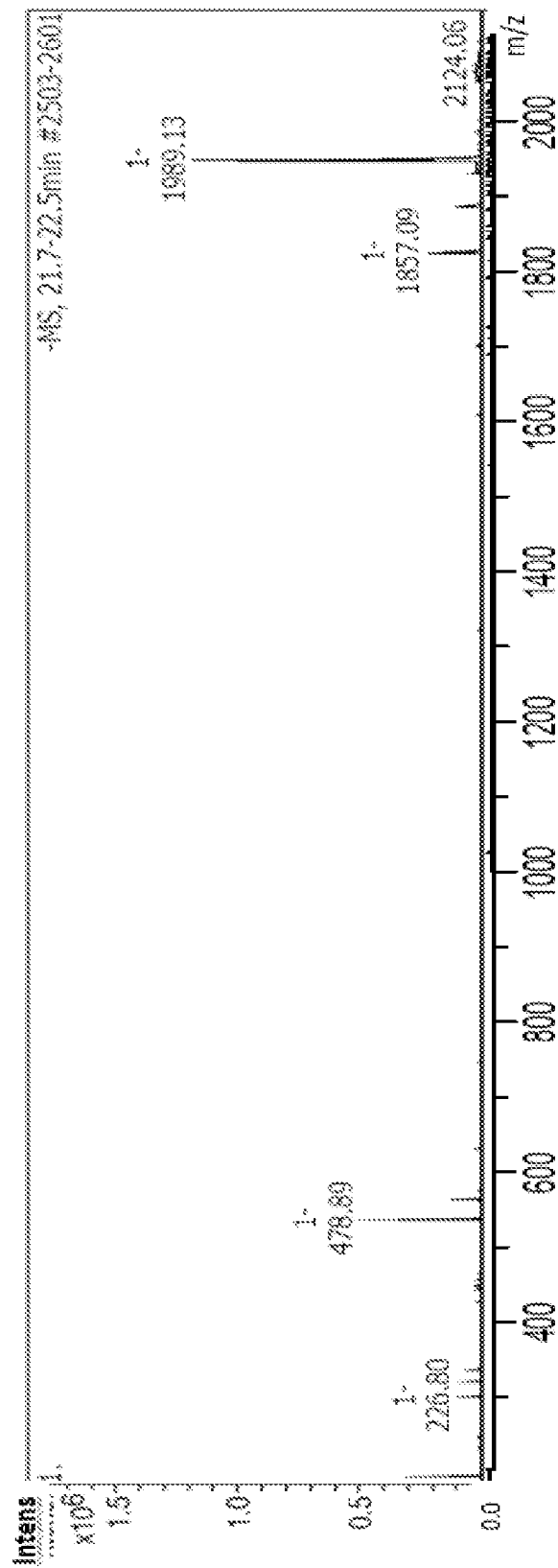

FIG. 5B and the mass peak at 1857.09 illustrate the presence of compounds with a molecular weight about 1857. The mole ratio of compounds with a molecular weight about 1857 are: 10.2% in FIG. 5A, 3.2% in FIG. 5B and 13% in FIG. 5C.

Figure 6:
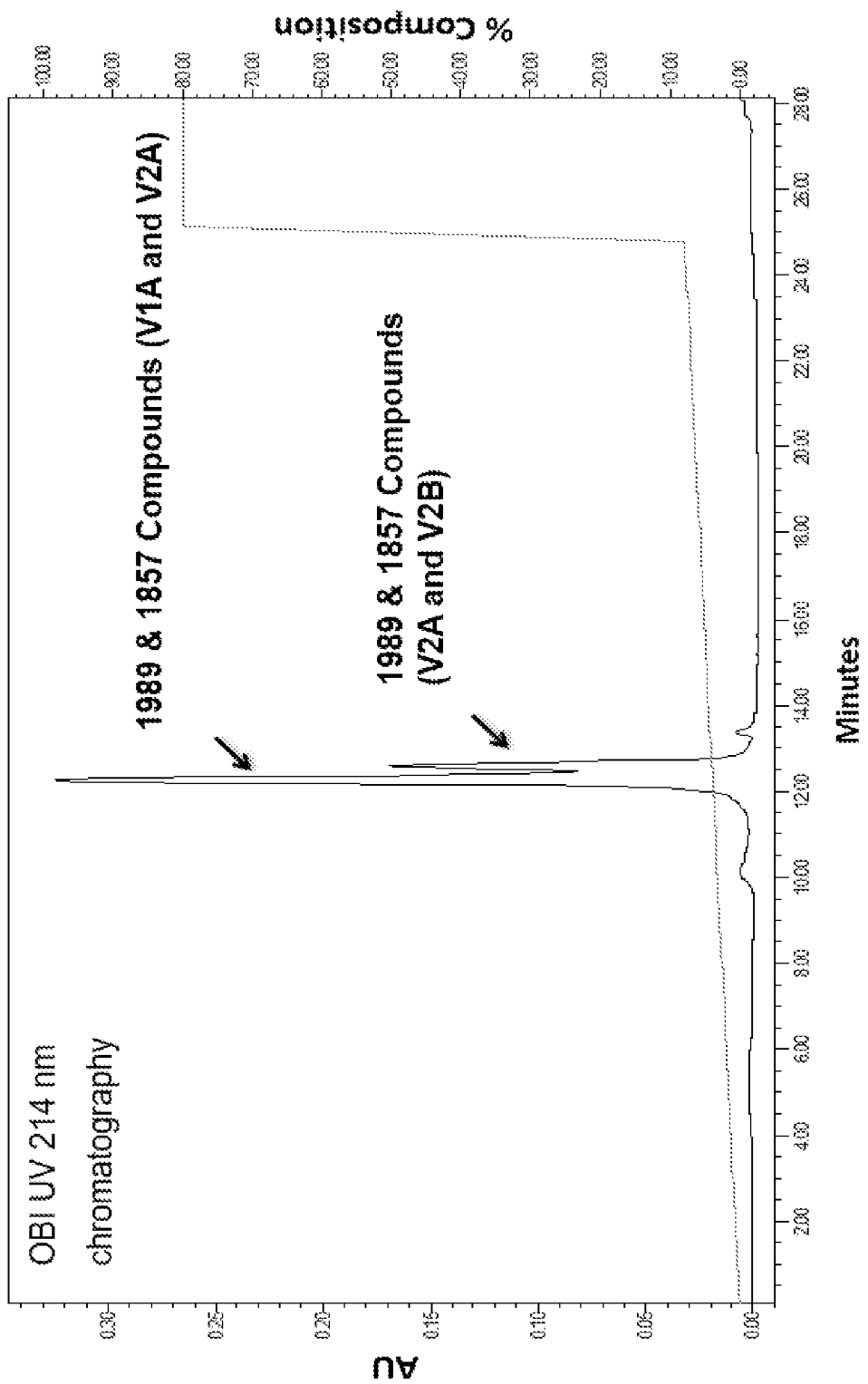
FIG. 6 is a chromatogram LC-UV image of OBI-821.
Figure 7:
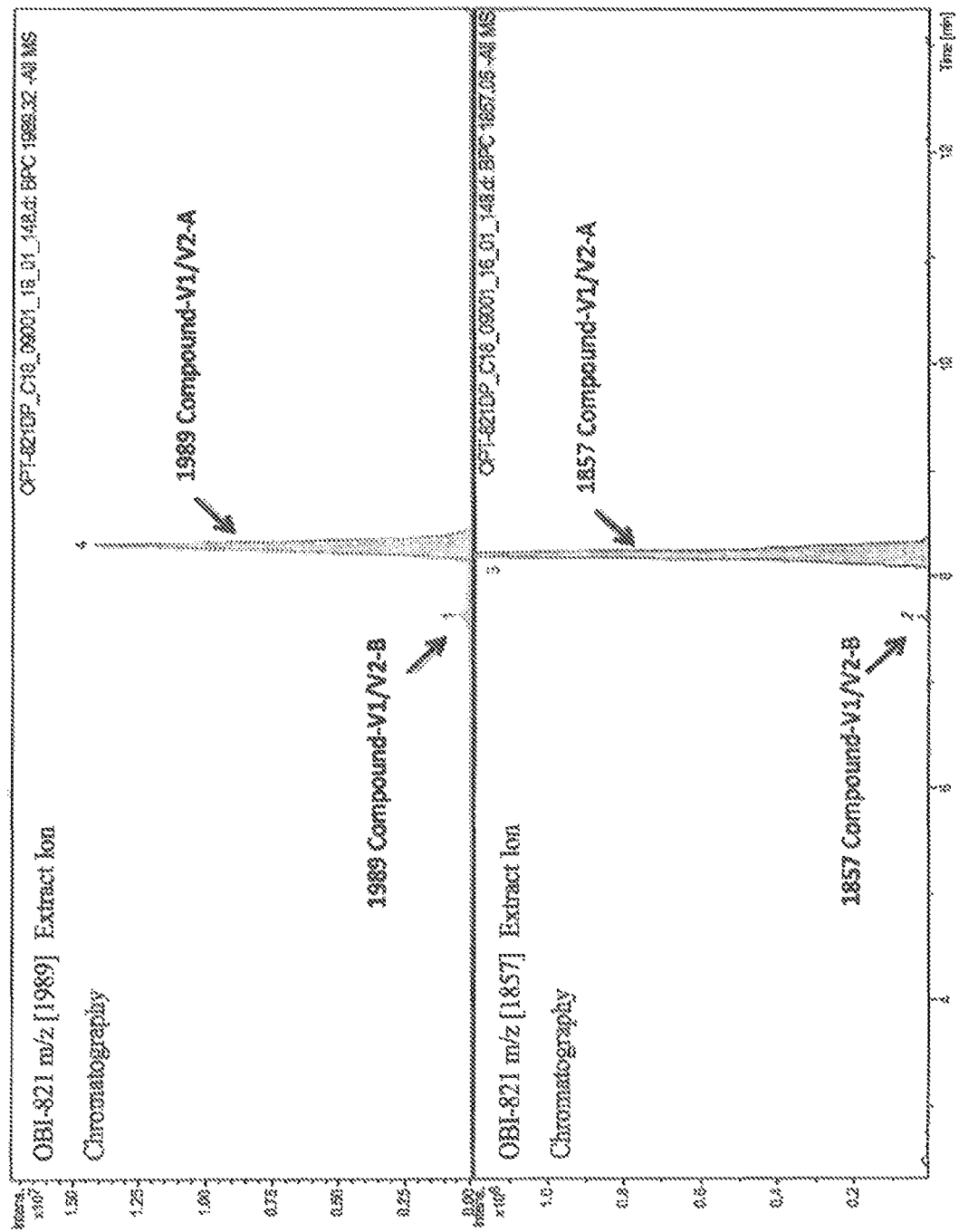
FIG. 7 is an assembly of chromatogram LC-MS images of OBI-821.

Purified OBI-821 saponin was further analyzed by chromatography. FIG. 6 is a chromatogram LC-UV image (Column: PolyLC PolyHYDROXYETHYL A 200*4.6 mm 5 um, 300A). The first peak illustrates the presence of 1989 V1 (A & B) compounds and 1857 compounds V1 (A & B) compounds (about 65.94%), and the second peak illustrates the presence of 1989 V2 (A & B) compounds and 1857 V2 (A & B) compounds (about 34.06%). FIG. 7 is a chromatogram LC-MS image (Column: Waters Symmetry ODS 150*2.1 mm). Peak 1 in the top panel illustrates the presence of 1989 compound V1B and V2B (about 2.2%), whereas Peak 4 illustrates the presence of 1989 compound V1A and V2A (about 97.8%). Peak 2 in the lower panel illustrates the presence of 1857 compound V1 B and 1857 compound V2 B (about 1.9%) and Peak 3 illustrates the presence of 1857 compound V1A and 1857 compound V2A.

Example 2: Immunogenicity of Vaccines with Higher Carbohydrate/Toxin Protein Ratio and Adjuvant Efficacy of OBI-281 Saponin An in vivo immunogenicity evaluation of Globo H/DT (8:1) vaccine in Example 1 and the adjuvant efficacy of OBI-821 saponin was performed using CL57B/6 mice.

CL57B/6 mice of approximately eight weeks old were randomized into the following 4 study groups:

| Group | Treatment | N (number of mice) | Route of administration | Day of immunization |
|---|---|---|---|---|
| Globo H-DT/S | Globo H/KLH/OBI-821 saponin | 6 | subcutaneous | Day 0, 7, 14 and 21 |
| Globo H-KLH/C34 | Globo H/KLH/C34 | 6 | | |
| Globo H-DT/S | Globo H/DT(ratio of molecules of Globo H to DT = 8:1)/OBI-821 saponin | 6 | | |
| Globo H-DT/C34 | Globo H/DT(ratio of molecules of Globo H to DT = 8:1)/C34 | 6 | | |

Preparation of OBI-821 Saponin
OBI-821 saponin was extracted from *Quillaja saponaria* extract accordingly to the following steps:
(a) *Quillaja saponaria* extract was pre-filtered by large particle C18 reverse phase chromatography, then purified by silica based preparative normal phase chromatography. This resulted in crude OBI-821.
(b) The crude OBI-821 in Step (a) was again pre-filtered by a large particle C18 reverse phase chromatography, followed by reverse phase preparative HPLC. OBI-821 substance was finished sequentially by desalting and lyophilization process.

Figure 1B:
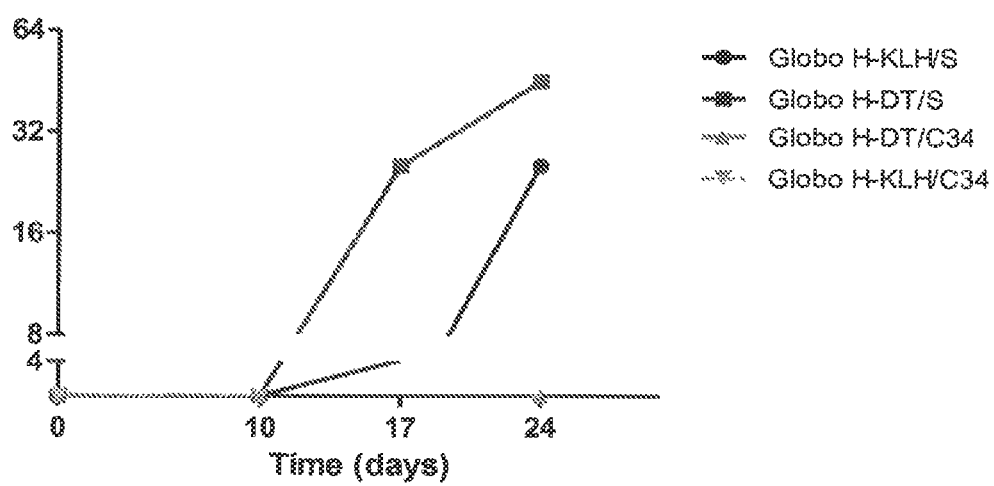
FIG. 1B is a line plot illustrating the Anti-Globo H IgG titer over a 24-day period of the compositions in FIG. 1A.

Purified OBI-821 saponin extracted from the bark of the *Quillaja saponaria* Molina tree was analyzed by mass spectrum. The mass peak at 1989.01 in FIG. 5A, the mass peak at 1989.12 in FIG. 5B and the mass peak at 1989.13 illustrate the presence of compounds with a molecular weight about 1989. The mole ratio of compounds with a molecular weigh about 1989 are: 89.8% in FIG. 5A, 96.8% in FIG. 5B and 87.0% in FIG. 5C. Similarly, the mass peak at 1856.97 in FIG. 5A, the mass peak at peak at 1856.02 in Blood samples were collected through retro-orbital or facial vein without anticoagulant prior to the first injection or Day 0, and three days after each injection (i.e., on Day 10, 17 and 24). Blood samples were centrifuged to separate serum and blood cells. Sera were collected and stored at −20° C., which were later analyzed by ELISA. Serum from each mouse was diluted serially for anti-Globo H IgG analysis. Globo H-ceramide was coated on assay plate overnight before blocked for 30 minutes with 1× blocking buffer (Sigma) and washed with PBST. Diluted serum samples were added to assay plate, incubated for 1 hr at room temperature (RT) and washed. Goat anti-mouse IgG-AP secondary antibody (Southern Biotech) was added to the sample and incubated for 45 minutes at RT. Plate was washed again, followed by the addition of chromogen substrate and incubation at 37° C. for 20 minutes. The reaction was terminated by adding a stop solution. The optical density was quantified by a plate reader (Molecular Device) at 405 nm wavelength. Mann-Whitney t-test was used for statistical analysis. FIG. 1A and FIG. 1B show the quantitative Anti-Globo H IgG titer of the tested vaccines.

Results: The IgG titer from Globo H/DT (ratio 8:1)-immunized mice was significantly higher than that of Globo H/KLH with a C34 adjuvant (P<0.01). The IgG titer from Globo H/DT (ratio 8:1)-immunized mice was higher than that of Globo H/KLH with an OBI-821 saponin adjuvant. (see FIG. 1(A). Regardless of the type of carrier protein used, the OBI-821 saponin elicited a statistically significant higher IgG titer compare to the C34 adjuvant (P<0.05, see FIG. 1A and FIG. 1B).

Example 3: Immunogenicity Evaluation of Vaccines with a Higher Carbohydrate/Toxin Protein Ratio and Adjuvant Efficacy of OBI-281 Saponin Using ADCC and CDC Assays Four groups of Lewis rats were immunized with the vaccines in Table 3.

TABLE 3

Vaccine Composition

| Groups | Vaccine compositions |
| --- | --- |
| G1 | Phosphate buffered saline (PBS) |
| G2 | 7.5 µg GH-DT(8:1 ratio of molecules of Globo H to DT) |
| G3 | 7.5 µg GH-DT(8:1 ratio of molecules of Globo H to DT) + 25 µg OBI-821 saponin |
| G4 | 7.5 µg GH-DT(24:1 ratio of molecules of Globo H to DT) + 25 µg OBI-821 saponin |

The rats were immunized s.c. with the vaccines listed in Table 3 on day 0, 7, 14, and 21. Peripheral blood mononuclear cells (PBMC) and plasma were collected prior to the first injection (i.e. day 0) and on Day 10, Day 17 and Day 24.

ADCC and CDC assays were performed using a Calcein AM release method known in the art. The procedure is described as follows:

Target Cell Labeling with Calcein AM

MCF-7 breast cancer cells (target cells) were cultured in Minimum Essential Medium supplemented with 2 mM L-glutamine, 1 mM sodium pyruvate and 0.01 mg/mL insulin, 10% fetal bovine serum. The target cells were added to 96 well plates ($5 \times 10^3$ cells per well), and incubated at 37° C. in a humidified 5% $CO_2$ atmosphere overnight. The medium was discarded and each well was washed once with PBS. 100 L of 20 M Calcein-AM solution was added into each well (2 nmole per well) and incubated at 37° C. in a humidified 5% $CO_2$ atmosphere for 2 hour. The supernatant was dried and each well was washed three times with PBS.

Target Cell Incubated with Sample Plasma

Sample plasma was heat-inactivated and 50 L of 1/5× heat-inactivated sample plasma was added into each well, except for the "Total release" and "Background" control. The final dilution fold would be 1/10× after the addition of 50 L of PBMC or serum. The plates were incubated at 37° C. (in dark) for 30 min.

Target Cell Incubated with PBMC or Complement

After incubation, 50 microliter of PBMC ($2 \times 10^6$ cells/mL) (for E:T ratio:20:1) were added to each well in the ADCC assay, and 50 microliter of 1/10× diluted serum was added to each well in the CDC assay, except for the "Total release" and "Background" control. The mixtures of reaction were incubated at 37° C. in a humidified 5% $CO_2$ atmosphere for 4 hour. The phenol-red free MEM containing 2% Triton solution (50 microliter) was added to the "Total release" control at the last 15 min of incubation time, and the phenol-red free MEM (50 microliter) was added to the "Background" control. The plates were centrifuged at 100 g for 5 min and then the supernatant 80 microliter was transferred to 96-well black plates. The fluorescence was measured at 485 nm excitation and 538 nm emission wavelengths.

FIGS. 2A to 2D show the in vivo ADCC and CDC activities of G2, G3 and G4 vaccines.

Figure 2A:
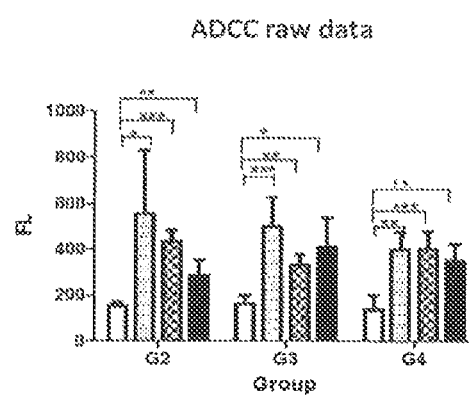
FIGS. 2A-2D is an assembly of bar graphs showing in vivo ADCC and CDC activities of G2 vaccine (Globo H/DT (8:1)); G3 vaccine (Globo H/DT (8:1)/OBI-821); and G4 vaccine (Globo H/DT (24:1)/OBI-821) in mice over a 24-day period.
Figure 2B:
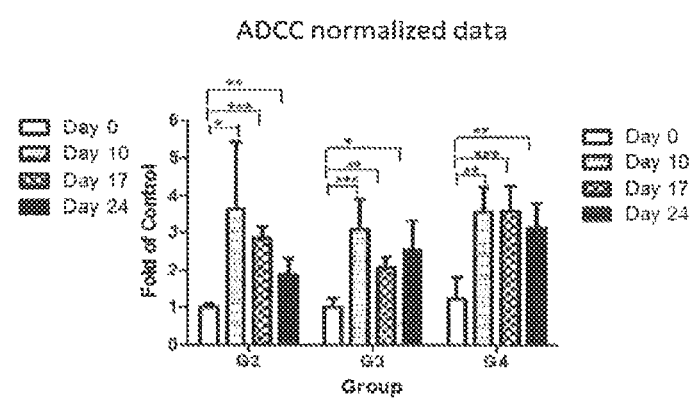
Figure 2C:
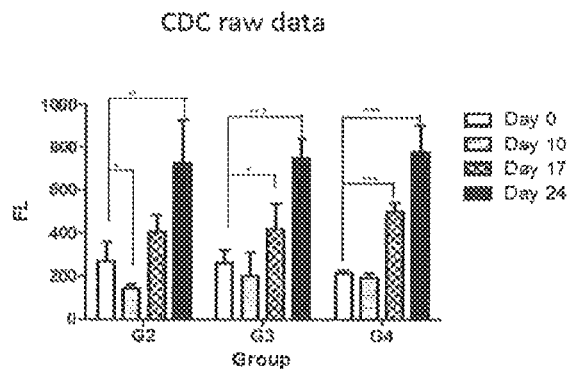
Figure 2D:
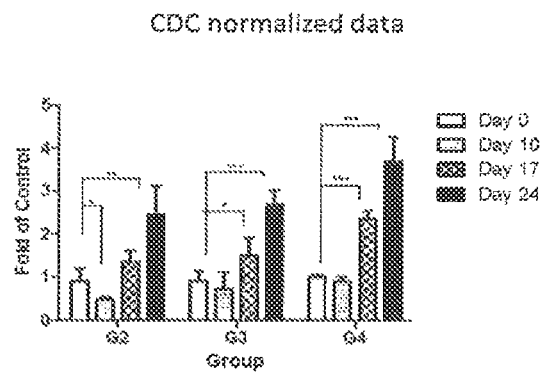

Results: As illustrate in FIGS. 2B and 2D, ADCC and CDC activities of G3 vaccine (with a OBI-821 saponin adjuvant) on Day 24 were higher than those of G2 vaccine (without a saponin advjuant). As illustrated in FIGS. 2B and 2D, ADCD and CDC activities of G4 vaccine (Globo H/DT ratio is 24:1) on Day 24 were higher than those of G3 vaccine (Golbo H/DT ratio is 8:1). These results show that OBI-821 saponin adjuvant and a vaccine with a carbohydrate antigen/toxin protein ratio over 5:1 enhance and induce longer lasting ADCC and CDC response.

Example 4: Immune Response of Vaccines with a Higher Carbohydrate/Toxin Protein Ratio and Adjuvant Efficacy of OBI-821 Saponin An in vivo evaluation of Globo H/DT (8:1) and Globo H/DT (16:1) vaccines in Example 1 and OBI-821 saponin adjuvant was performed using CL57B/6 mice or Balb/c mice.

CL57B/6 mice of approximately eight weeks old were randomized into the following 8 study groups:

| Group | Treatment | N (number of mice) | Immunization Dose and Schedule |
| --- | --- | --- | --- |
| G1 | Globo H/KLH/OBI-821 saponin | 6 | 2 × s.c. injections on Day 0, 7, 14, and 21. Each injection is 100 uL |
| G2 | Globo H/DT(3:1 ratio of molecules of Globo H to DT)/OBI-821 saponin | 6 | |
| G3 | H/DT(8:1)/OBI-821 saponin | 6 | |
| G4 | Globo H/DT(8:1 ratio of molecules of Globo H to DT)/OBI-821 saponin | 6 | |
| G5 | Globo H/DT(8:1 ratio of molecules of Globo H to DT)/C34 | 6 | |
| G6 | Globo H/KLH/C34 | 6 | |
| G7 | Globo H/DT(16:1 ratio of molecules of Globo H to DT)/OBI-821 saponin | 6 | |
| G8 | PBS (Phosphate Buffered Saline) | 3 | |

Figure 3A:
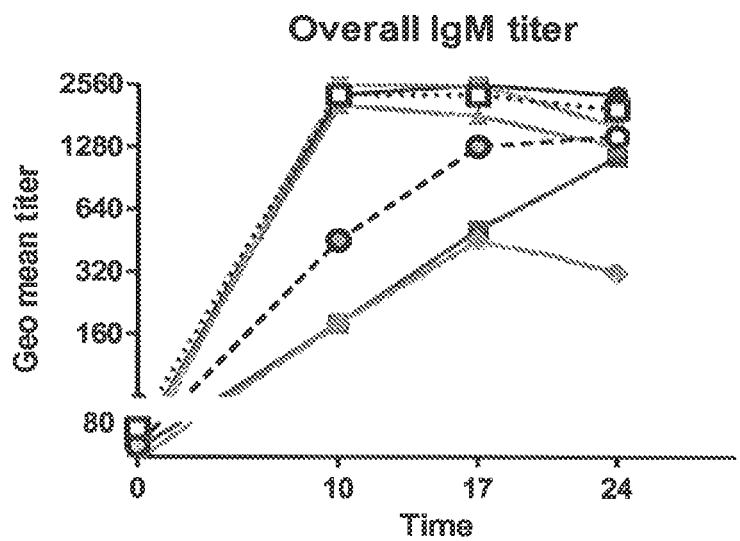
FIG. 3A and FIG. 3 B are line plots illustrating the overall IgM and IgG titers of the following compositions over a 24-day period: G1 (Globo H/KLH/OBI-821), G2 (Globo H/DT (3:1)/OBI-821), G3 and G4 (Globo H/DT (8:1)/OBI-821), G5 (Globo H/DT (8:1)/C34), G6 (Globo H/KLH/C34), G7 (Globo H/DT(16:1)/OBI-821) and G8 (PBS).
Figure 3B:
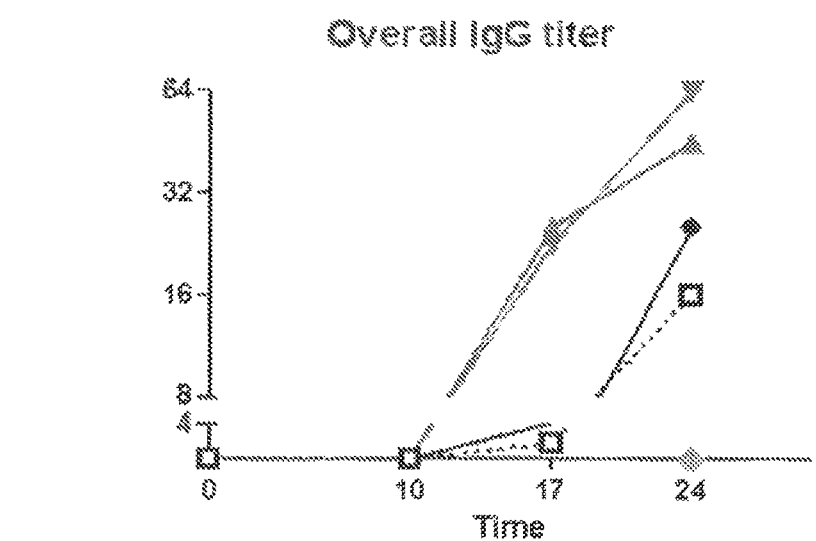
Figure 4A:
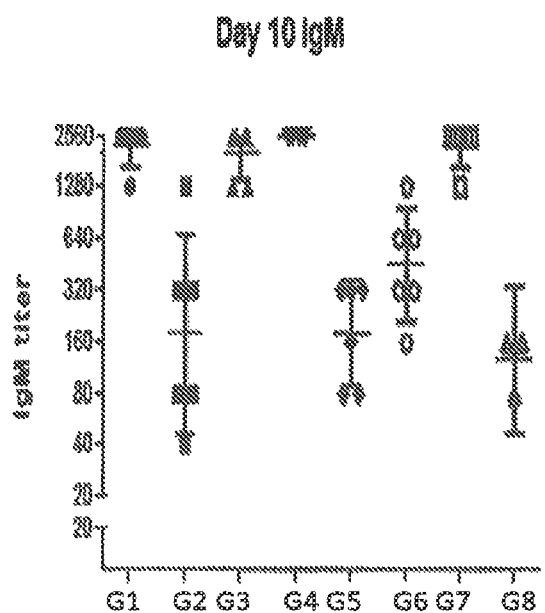
FIGS. 4A-4F is an assembly of bar graphs showing the IgM and IgG response at Day 10, Day 17 and Day 24 of the compositions listed in FIG. 3: Panel (A)-(C) illustrate the IgM response of the compositions listed in FIG. 3. on day 10, 17 and 24 respectively. Panel (D)-(F) illustrate the IgG response of the compositions listed in FIG. 3 on day 10, 17 and 24 respectively.
Figure 4B:
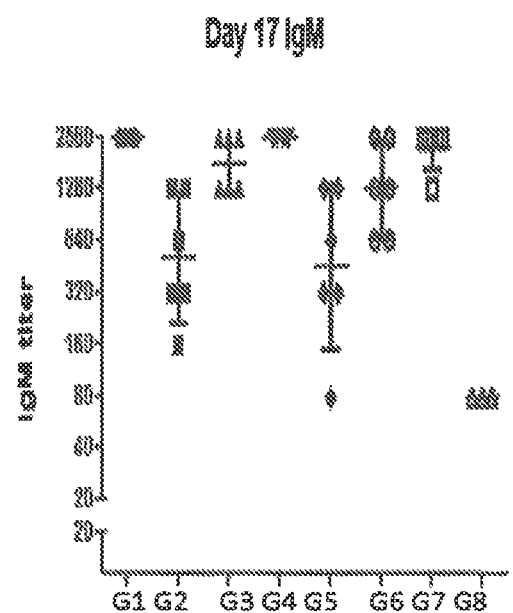
Figure 4C:
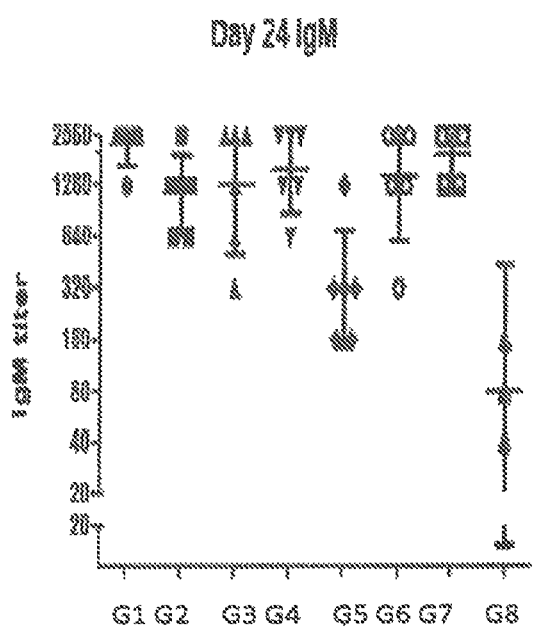
Figure 4D:
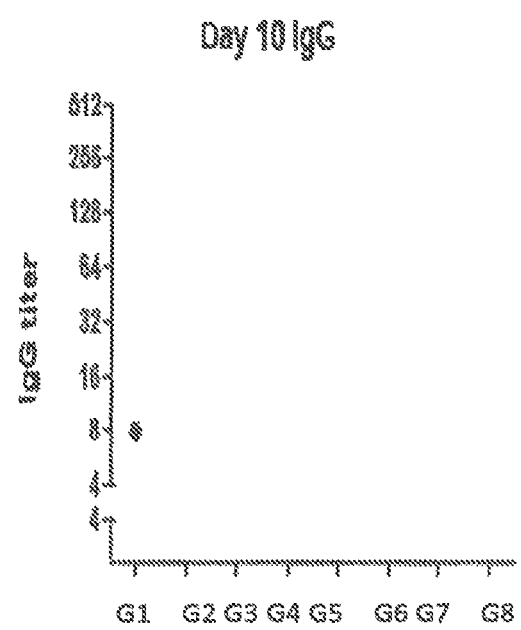
Figure 4E:
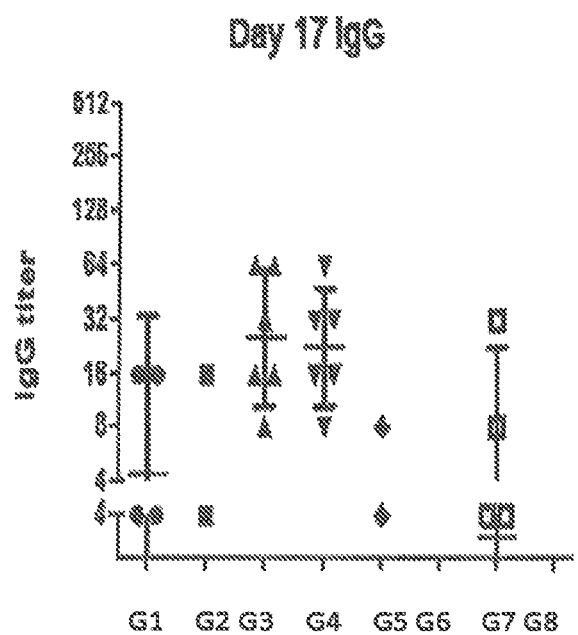
Figure 4F:
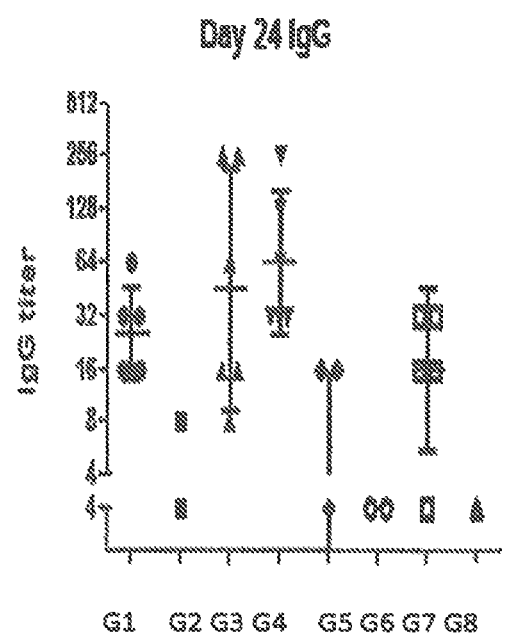

Blood samples were collected through retro-orbital or facial vein without anticoagulant prior to the first injection or Day 0, Day 10, 17 and 24. Blood samples were centrifuged to separate serum and blood cells. Sera were collected and stored at −20° C., which were later analyzed by ELISA. Serum from each mouse was diluted serially for anti-Globo H IgG and IgM analysis. FIG. 3A, FIG. 3B and FIG. 4 show the quantitative Anti-Globo H IgM and Anti-Globo H IgG titer of the tested vaccines.

Results: Vaccines with an OBI-821 saponin adjuvant induce a statistically significant more Anti-Globo H IgM and Anti-Globo H IgG compare to vaccines with a C34 adjuvant (See FIG. 3A, FIG. 3B and FIG. 4). The following statistical significant differences were noted:

IgM titer of G3 vaccine (OBI-821 saponin) was significantly higher than that of G5 vaccine (C34) on Day 17 ($p=0.02$);
  IgM titer of G1 vaccine (OBI-821 saponin) was significantly higher than that of G6 vaccine (C34) on Day 17 ($p=0.03$), IgM titer of G3 vaccine (OBI-821 saponin) was significantly higher than that of G5 vaccine (C34) on Day 24 (p=0.03), IgG titer of G3 vaccine (OBI-821 saponin) was significantly higher than that of G5 vaccine (C34) on Day 17 (p=0.001), IgG titer of G1 vaccine (OBI-821 saponin) was significantly higher than that of G6 vaccine (C34) on Day 17 (p=0.003), IgG titer of G3 vaccine (OBI-821 saponin) was significantly higher than that of G5 vaccine (C34) on Day 24 (p=0.03), and IgG titer of G1 vaccine (OBI-821 saponin) was significantly higher than that of G6 vaccine (C34) on Day 24 (p=0.004).

These results illustrate that OBI-821 saponin adjuvant significantly enhances IgM and IgG response compare to C34 adjuvant.

Globo H/KLH/OBI-821 Saponin (G1) induces a significantly higher IgM and IgG titers compare to Globo H/DT (3:1)/OBI-821 Saponin (G2) on Day 17 and Day 24. Without being bound by a particular theory, it is believed that G1 has a higher carbohydrate density (about 700 Glob H units per KLH carrier protein) and elicited a stronger immune response whereas G2 has a lower carbohydrate density (3 Globo H units per DT carrier protein) and elicited a weaker immune response. The following statistical significant differences were noted:

IgM titer of G1 vaccine (KLH) was significantly higher than that of G2 vaccine (DT) on Day 17 (p=0.003), IgM titer of G1 vaccine (KLH) was significantly higher than that of G2 vaccine (DT) on Day 24 (p=0.03), IgG titer of G1 vaccine (KLH) was significantly higher than that of G2 vaccine (DT) on Day 24 (p=0.004).

IgM and IgG titers of Globo H/DT (8:1—ratio of molecules of Globo H to DT)/OBI-821 Saponin (G3 and G4) and Globo H/DT(16:1—ratio of molecules of Globo H to DT)/OBI-821 Saponin (G7) are comparable to those of Globo H/KLH/OBI-821 Saponin (G1) on Day 17 and Day 24. (See FIG. 4). Despite lower carbohydrate density than GH-KLH (700:1—ratio of molecules of Globo H to DT), GH-DT(8:1—ratio of molecules of Globo H to DT) exhibited comparable immunogenicity with GH-KLH.

Vaccines with higher Globo H/DT ratio (8:1 or 16:1—ratio of molecules of Globo H to DT) induce a higher and longer lasting IgM and IgG titers compare to vaccine with a lower Globo H/DT ratio (3:1). The following statistical significant differences were noted:

IgM titer of G3 vaccine (8:1 ratio—ratio of molecules of Globo H to DT) was significantly higher than that of G2 vaccine (3:1 ratio) on Day 17 (p=0.02), IgM titer of G7 vaccine (16:1 ratio—ratio of molecules of Globo H to DT) was significantly higher than that of G2 vaccine (3:1 ratio) on Day 17 (p=0.006), IgG titer of G3 vaccine (8:1 ratio—ratio of molecules of Globo H to DT) was significantly higher than that of G2 vaccine (3:1 ratio) on Day 17 (p=0.01), IgG titer of G7 vaccine (16:1 ratio—ratio of molecules of Globo H to DT) was significantly higher than that of G2 vaccine (3:1 ratio—ratio of molecules of Globo H to DT) on Day 17 (p=0.03), IgG titer of G3 vaccine (8:1 ratio—ratio of molecules of Globo H to DT) was significantly higher than that of G2 vaccine (3:1 ratio) on Day 24 (p=0.01), IgG titer of G7 vaccine (16:1 ratio—ratio of molecules of Globo H to DT) was significantly higher than that of G2 vaccine (3:1 ratio—ratio of molecules of Globo H to DT) on Day 24 (p=0.01), IgG titer of Globo H/DT (8:1—ratio of molecules of Globo H to DT)/OBI-821 Saponin (G3) and Globo H/DT (16:1)/OBI-821 Saponin (G7) are significantly higher than that of Globo H/DT(3:1—ratio of molecules of Globo H to DT)/OBI-821 Saponin (G2) on Day 17 and 25 (P<0.05).

All publications, patents, and patent applications cited in this specification are herein incorporated by reference as if each individual publication or patent application was specifically and individually indicated to be incorporated by reference.

The present invention is not to be limited in the scope of the embodiments disclosed herein, which are intended as single illustrations of individual aspects of the invention, but not limitation to the scope of the invention. Various modifications to the models and methods of the invention, in addition to those described herein, will become apparent to those skilled in the art from the foregoing description and teachings, and are similarly intended to fall within the scope of the invention. Such modifications or other embodiments can be practiced without departing from the true scope and spirit of the invention.

What is claimed is:

1. A saponin mixture comprising:
(i) 1 to 15 mole % of a 1857 compound mixture, wherein the 1857 compound mixture comprises each of the following isolated compound of formula (I):

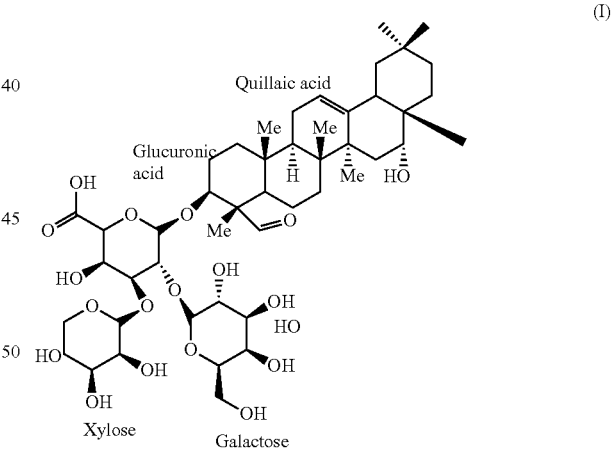

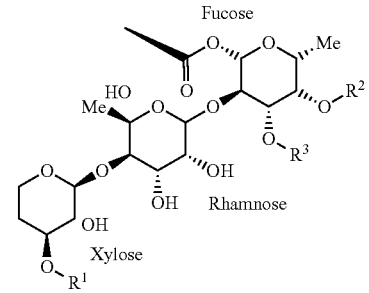

(a) wherein $R^1$ is β-D-Apiose, $R^2$ is

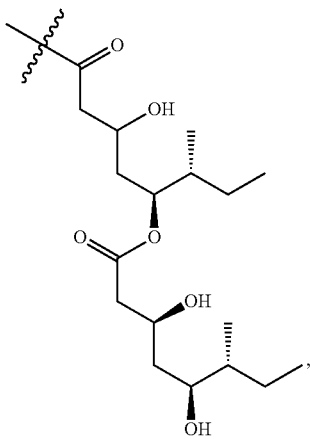 [SMILES: *C(=O)CC(O)C[C@H](OC(=O)C[C@@H](O)C[C@H](O)[C@H](C)CC)[C@H](C)CC]

and $R^3$ is H the 1857 compound V1A;

(b) wherein $R^1$ is β-D-Apiose, $R^2$ is H, and $R^3$ is

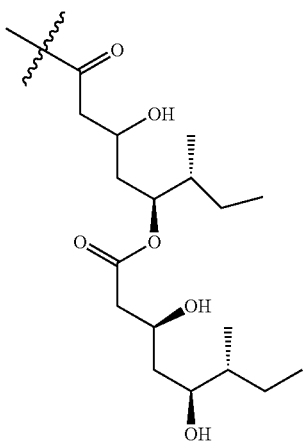 [SMILES: *C(=O)CC(O)C[C@H](OC(=O)C[C@@H](O)C[C@H](O)[C@H](C)CC)[C@H](C)CC]

the 1857 compound V1B;

(c) wherein $R^1$ is β-D-Xylose, $R^2$ is

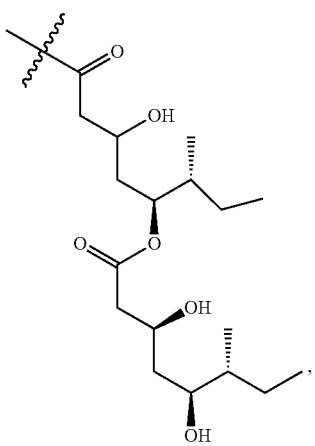 [SMILES: *C(=O)CC(O)C[C@H](OC(=O)C[C@@H](O)C[C@H](O)[C@H](C)CC)[C@H](C)CC]

and $R^3$ is H, the 1857 compound V2A; and (d) wherein $R^1$ is β-D-Xylose, $R^2$ is H, and $R^3$ is

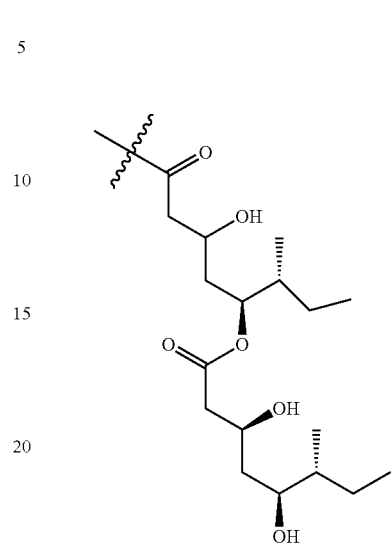

the 1857 compound V2B; and (ii) 85 to 99 mole % of a 1989 compound mixture, wherein the 1989 compound mixture comprises each of the following isolated compound of formula (I):

(a) wherein $R^1$ is β-D-Apiose, $R^2$ is

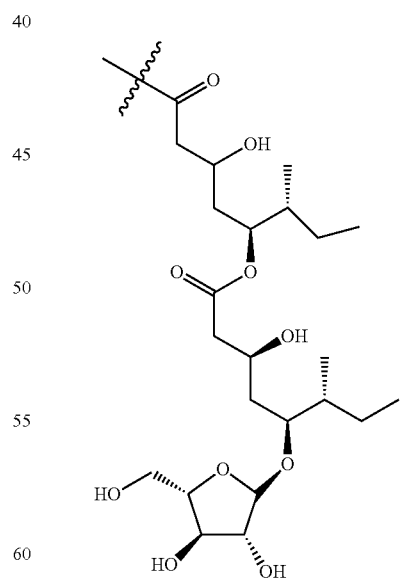

and $R^3$ is H, the 1989 compound V1B;

(b) wherein $R^1$ is β-D-Apiose, $R^2$ is H, and $R^3$ is

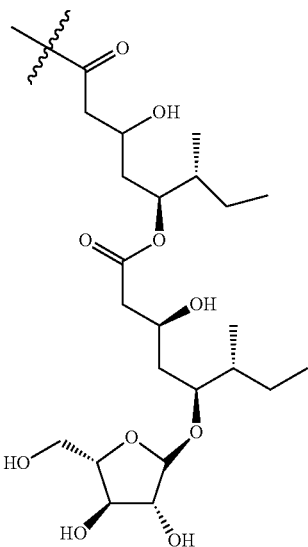

the 1989 compound V2A;

(c) wherein $R^1$ is β-D-Xylose, $R^2$ is

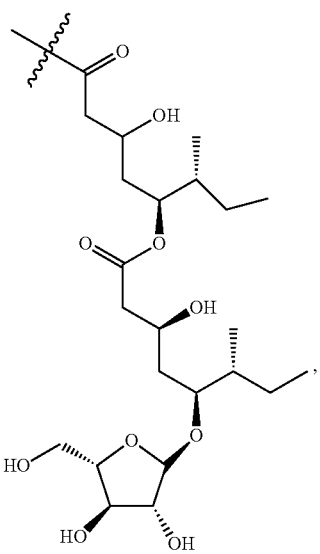

and $R^3$ is H, the 1989 compound V2B; and (d) wherein $R^1$ is β-D-Xylose, $R^2$ is H, and $R^3$ is

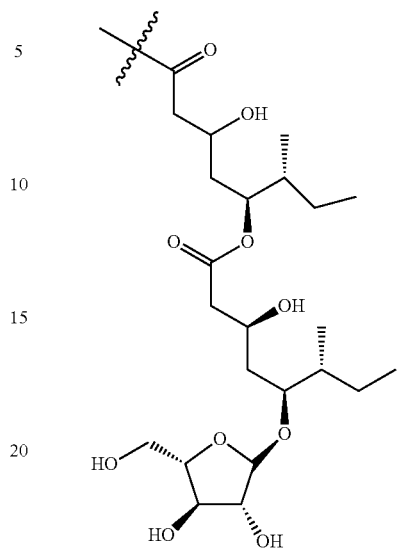

the 1989 compound V2B,
wherein the 1857 compound mixture comprises about 60-70 mole % of the 1857 compound V1A; 1-5 mole % of the 1857 compound V1B, about 30-40 mole % of the 1857 compound V2A, and 0.1-3 mole % of the 1857 compound V2B; and
wherein the 1989 compound mixture comprises about about 60-70 mole % of the 1989 compound V1A, 1-5 mole % of the 1989 compound V1B, about 30-40 mole % of the 1989 compound V2A, and 0.1-3 mole % of the 1989 compound V2B.

2. A vaccine for the treatment of cancer, comprising:
(a) a tumor-associated carbohydrate antigen; and
(b) the saponin mixture of claim 1.

3. The vaccine of claim 2, wherein the tumor-associated carbohydrate antigen is Globo H.

4. The vaccine of claim 2, wherein the cancer is Globo H expressing cancer.

5. The vaccine of claim 4, wherein the Globo H expressing cancer is selected from the group consisting of breast cancer, lung cancer, esophageal cancer, rectal cancer, biliary cancer, liver cancer, buccal cancer, gastric cancer, colon cancer, nasopharyngeal cancer, kidney cancer, prostate cancer, ovarian cancer, cervical cancer, endometrial cancer, pancreatic cancer, testicular cancer, bladder cancer, head and neck cancer, oral cancer, neuroendocrine cancer, adrenal cancer, thyroid cancer, bone cancer, skin cancer, basal cell carcinoma, squamous cell carcinoma, melanoma, and brain tumor.

* * * * *